United States Patent [19]

Stern

[11] 4,150,495
[45] Apr. 24, 1979

[54] LEL (LOWER EXPLOSIVE LIMIT) CONTROL WITH AUTOMATIC CALIBRATION CAPABILITY

[75] Inventor: Nathan Stern, Caldwell, N.J.
[73] Assignee: Bobst-Champlain, Inc., Roseland, N.J.
[21] Appl. No.: 902,551
[22] Filed: May 3, 1978
[51] Int. Cl.² ............... F26B 21/06; G01N 27/16
[52] U.S. Cl. ............................. 34/54; 34/89; 73/1 G; 73/23; 101/416 A
[58] Field of Search ............ 73/23, 1 G; 101/416 A; 34/89, 54, 34, 29, 155; 432/37, 45

[56] References Cited

U.S. PATENT DOCUMENTS

| 3,791,049 | 2/1974 | Smith, Jr. | 34/54 |
| 3,811,201 | 5/1974 | Endter et al. | 34/54 |
| 3,924,442 | 12/1975 | Kerho et al. | 73/23 |

FOREIGN PATENT DOCUMENTS 536905  5/1941  United Kingdom ............... 101/416 A Primary Examiner—Stephen A. Kreitman
Attorney, Agent, or Firm—James & Franklin

[57] ABSTRACT

The LEL (Lower Explosive Limit) control includes a gas analyzer normally connected to receive sample gas from the evaporation enclosure of a press dryer section and which, during calibration, is sequentially connected to first analyze solvent free gas and then gas having a known solvent content. Situated with the analyzer is a detector the resistance of which changes in proportion to the temperature within the flame cell of the analyzer. The detector forms a portion of a bridge circuit, which also includes a potentiometer. The output of the bridge is amplified, compared to a selected reference voltage and a signal representing the difference therebetween is processed. The processed signal is combined with a signal representing the web speed to form a resultant signal to control a pneumatically operated damper in the enclosure exhaust conduit. Automatic calibration of the system is initiated periodically and takes place in two phases. During the first phase of calibration, the potentiometer is set in accordance with the difference between the amplifier output derived from analysis of the solvent free gas and a 0% reference voltage. During the second phase of calibration, the gain of the bridge output amplifier is set in accordance with the difference between the amplifier output derived from the analysis of the known solvent concentration gas and a full scale reference voltage. When calibration is taking place, the output of the comparison circuit is inhibited and the damper position is determined in accordance with the web speed alone. Emergency stop of the press occurs when the output of the amplifier exceeds a given level.

45 Claims, 16 Drawing Figures

LEL (LOWER EXPLOSIVE LIMIT) CONTROL WITH AUTOMATIC CALIBRATION CAPABILITY

The present invention relates to the LEL (lower explosive limit) controls and more particularly to an LEL control having automatic periodic calibration capability.

LEL controls of a variety of different structures are well known in the art. Such controls are commonly utilized as energy saving devices and as failsafe mechanisms in the dryer sections of printing presses or the like and, therefore, the present invention will be described in this context.

In a printing press, after the ink solution has been deposited on the web, the web is passed through a dryer. The dryer includes an enclosure wherein heated air is passed over the web to evaporate the solvent from the deposited ink solution. The evaporated ink solvent and air forms a potentially explosive mixture if the solvent concentration thereof is greater than a given level, commonly referred to as the lower explosive limit (LEL). In order to insure that the air within the evaporation enclosure does not contain a solvent concentration greater than the lower explosive limit and, therefore constitutes a safety hazard, it is possible to continuously withdraw all of the solvent laden air from the enclosure connected thereto. The solvent laden air is then transferred to a pollution control device which processes the exhaust prior to releasing same into the atmosphere.

The amount of energy required to operate the pollution control apparatus is proportional to the volume of exhaust which must be processed. If an LEL control is utilized to regulate the position of a damper located in the exhaust conduit, it is possible to accurately regulate the solvent concentration in the evaporation enclosure and therefore prevent the solvent concentration from exceeding a safe level. This may be achieved by recycling a regulated proportion of the solvent laden air to the input side of the enclosure and by controlling the exhaust damper such that only a relatively small proportion of the solvent laden air is transferred to the pollution control apparatus. This method substantially reduces the amount of energy which is required to operate the pollution control apparatus because the amount of exhaust to be processed is substantially reduced. Thus, when used in this manner, the LEL control acts as an energy saving device.

In addition, the LEL control can be connected in a failsafe manner such that if the solvent level concentration within the evaporation enclosure rises above the lower explosive limit, this condition can be detected, an "emergency stop" signal generated and the press can be shutdown automatically. This will prevent further build up of the solvent concentration, possibly leading to a hazardous condition and will insure that any malfunction in the system will be corrected before an explosion takes place.

Because of the critical nature of the above-described functions, it is necessary that the LEL control operate accurately. In order to insure accuracy, calibration of the control is required on a frequent basis. Obviously, during the calibration period, which requires several minutes, the LEL control can not function to regulate the exhaust damper in accordance with the sensed solvent concentration level. Therefore, in prior art systems, calibration must take place when the press is not operating or the press must operate without control of the solvent concentration level during calibration.

Prior art systems regulate the position of the exhaust damper in accordance with the solvent concentration alone. Thus, in the event that the solvent concentration monitoring portion of the system fails, the press must be shut down or run in an uncontrolled manner. In order to avoid this problem, it would be advantageous to design a system which will operate in a "back up" mode which will take into account the worst case conditions and continue to regulate the solvent concentration at a net energy savings. This can be accomplished by positioning the exhaust damper in accordance with a signal proportional to the web speed. The press will therefore continue to run unless a dangerous solvent concentration occurs or the exhaust damper cannot respond to the control signal.

The intrinsic safety of LEL control is a matter of concern because of the environment in which the control operates. Some of the components, such as the reference gas sources and fuel sources for the gas analyzer and power supply can be located in a safe area. However, certain components must be located in the hazardous area. It is necessary to design the components located in the hazardous area in such a manner so as to prevent an explosion from occuring.

It is, therefore, a prime object of the present invention to provide an LEL control having automatic calibration capablity wherein the calibration cycle is automatically periodically initiated and during calibration the LEL level continues to be controlled, such that the safe operation of the press is uninterrupted.

A further object of the present invention is to provide an LEL control having automatic calibration capability wherein during the calibration cycle the system regulates the exhaust damper position in accordance with the speed of the web alone.

It is another object of the present invention to provide an LEL control having automatic calibration capability wherein an "emergency stop" signal is automtically generated in the event that the solvent concentration level exceeds a present value.

It is still further object of the present invention to provide an LEL control having automatic calibration capability wherein calibration takes place at both the zero solvent concentration level and at the full scale solvent concentration level.

It is still another object of the present invention to provide an LEL control having automatic calibration capability which will operate in an intrinsically safe manner.

In accordance with the present invention, the LEL control regulates the position of an exhaust damper associated with an evaporation enclosure through which a solvent laden web passes. The control includes means operably connected to the enclosure for sensing the solvent concentration therein and for generating a first signal proportional to the sensed solvent concentration. Means operably associated with the web are provided for sensing the web speed and for generating a second signal proportional thereto. The control means includes means for combining the first signal and the second signal to form a control signal. Also included are means for calibrating the first signal generating means, the calibrating means comprising means for inhibiting the output of the first signal generating means during calibration. Means are provided for regulating the position of the damper in accordance with the control signal.

The first signal generating means comprises a gas analyzer which is normally connected to receive sample gas from the dryer enclosure. The gas analyzer is also connected to a first source of a solvent free gas and a second source of a gas of known solvent concentration. During the first phase of calibration, first valve means connect the first gas source to the chamber and during the second phase of calibration, second valve means connect the second gas source to the chamber, such that calibration at 0% LEL and full scale LEL can be achieved.

The first signal generating means further comprises a resistance bridge and an amplification means connected to the output thereof. The bridge includes a variable resistance means, located in the flame cell to sense the temperature thereof and a potentiometer. Processing means are provided for processing the first signal including comparison means for comparing the amplifier output with a selected one of three voltages representing, respectively, a set LEL level, 0% LEL level and full scale LEL level. The output of the comparison means is partially processed and connected to an analog switch which serves to inhibit the output of the processing circuitry during calibration. When the system is not being calibrated, the output of the processing circuitry is combined with the second signal based on the web speed, to form the control signal. During calibration, the control signal is based on the second signal alone. The control signal is utlized to position a damper located in the exhaust conduit connected to the enclosure.

The system normally operates in the LEL mode wherein gas from the enclosure is analyzed and the output of the amplifier is a function of the solvent concentration in the enclosure. This output is compared to a set LEL voltage and a signal representing the difference therebetween is processed, the web speed signal added thereto and the result is used to control the position of the damper.

Calibration is automatically initiated by a timing circuit and takes place in two phases. During the first phase, the flame cell is connected to receive the solvent free gas, which is then analyzed. The output of the amplifier is compared to a 0% LEL reference voltage and the signal representation of the difference therebetween is utilized to adjust the resistance bridge for the correct zero setting. During the second phase of calibration, the gas of known solvent concentration is analyzed. The output of the amplifier is compared to a preset reference voltage and the signal representation of the difference therebetween is utilized to adjust the gain of the amplifier to the correct full scale setting.

While calibration is taking place, the analog switch inhibits the output of the first control signal processing circuitry and the damper is positional in accordance with the web speed signal alone. The web speed is derived from the output of a tachometer connected to the web.

The LEL control also includes means for monitoring the first signal and for generating an "emergency stop" signal when the first signal exceeds a given value. This signal is utilized to prevent further solvent accumulation by shutting down the press.

Preferably, the control means also comprises manually actuatable means to disable the first control signal generating means. Thus, it is possible to manually actuate the LEL control to regulate the damper position in accordance with the web speed alone.

In the event of a failure in the monitoring portion of the system, the control will regulate the solvent concentration in accordance with the web speed alone such that the press operatin will not be interrupted. The operation of the system in this mode still constitutes a net energy savings. An emergency stop will occur only for a dangerous solvent concentration in the dryer or if the exhaust damper cannot respond to its control signal.

The intrinsic safety of the control of the present invention is insured by locating the source of known solvent concentration gas, fuel supply for the gas analyzer and power supply assembly in a non-hazardous area. In the hazardous area, the components are designed such that a fault condition cannot produce a hot enough spark to ignite a solvent sample in its most easily ignitable mixture. The 115 VAC line voltage is isolated from the connections to the hazardous area. This is accomplished by selecting a transformer whose primary and secondary are separated by an insulating barrier, grounding its core and properly fusing its input. Further isolation is accomplished by having a ground plane separating all primary from all secondary voltages. The secondary voltage is then limited by the wire wound barrier resistors which will fail open for a fault condition. In addition, the relays, being inductive, are protected by redundant shunt diodes to dissipate the inductive kick when the relay is de-energized.

The gas analyzer itself is protected by enclosing all electrical components in explosion proof enclosures. The web tachometer input is isolated by passing same through a zener barrier. The motorized potentiometers, and the electrical to pressure transducer coil, are shunted with redundant resistors. All connecting cables are adequately separated and provided with safety shielding. In this manner, the control is designed in an intrisically safe manner.

To the accomplishment of the above and to such other objectives that may hereinafter appear, the present invention relates to an LEL control with automatic calibration capability, as described in the present specification and recited in the annexed claims, taken together with the accmpanying drawings where like numerals refer to like parts and in which:

Figure 1:
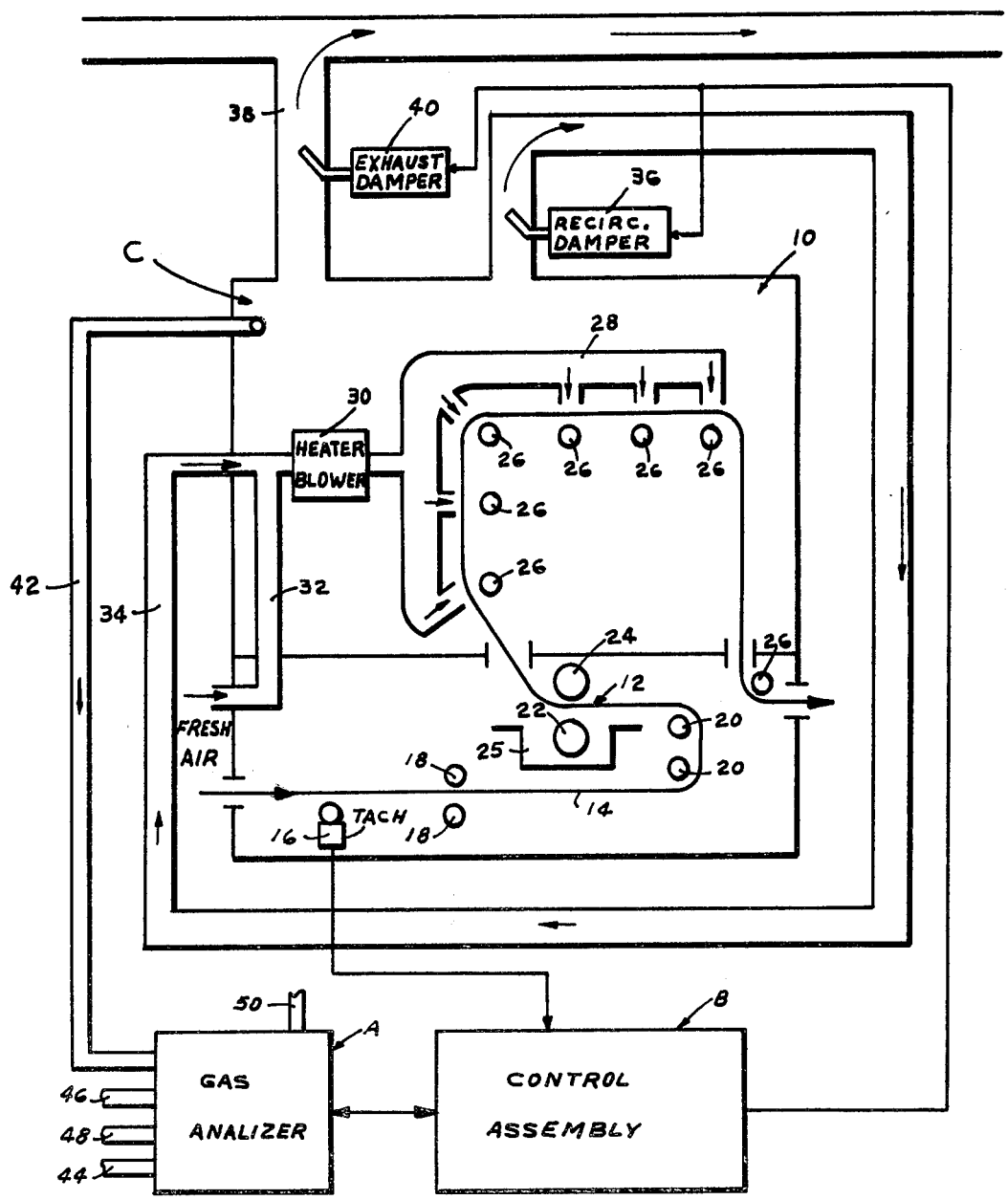
FIG. 1 is a schematic representation of the dryer section of a printing press showing the manner in which the LEL control of the present invention is connected thereto.

As shown in FIG. 1, the LEL Control of the present invention is associated with a gas analyzer, generally designated A, which is connected to the control assembly, generally designated B. The gas analyzer A and the control assembly B are shown as connected to a dryer section, generally designated C, of a printing press or the like. Dryer section C includes an evaporation enclosure 10 which is located directly above an inking station 12. As the web 14, which is to be imprinted, enters the inking station 12, it passes a tachometer 16, which can be any one of a variety of known commercially available tachometers designed for this purpose. Tachometer 16 measures the web speed and generates a signal proportional thereto. The web travels between idler rollers 18 and around idler rollers 20. Thereafter, the web passes between an inking roller 22 and a pressure roller 24. Inking roller 22 is partially immersed in an ink bath 25 and is provided with a plurality of indentations on the surface thereof which, after passage through ink bath 25, retain small amounts of the ink solution thereon. As the web 14 passes between inking roller 22 and pressure roller 24, the ink solution situated in the indentations on the surface of inking roller 22 is transferred to the surface of the web 14. Web 14 then travels into enclosure 10 and around idler rollers 26. After completing the path of travel through enclosure 10, the web exits the other side thereof and is transferred to the next printing section.

Adjacent to idler rollers 26, but spaced therefrom to permit web 14 to pass therebetween, is a duct 28 having a plurality of outlet openings situated in close proximity to the suface of web 14. Duct 28 is fed from a heater/-blower apparatus 30. The input side of heater/blower apparatus 30 is connected to a fresh air inlet conduit 32 and a recirculation conduit 34. Recirculation conduit 34 originates at the top of enclosure 10 and the amount of solvent laden air which is recirculated from enclosure 10 to heater/blower apparatus 30 is regulated by a recirculation damper 36 located near the entrance of the recirculation conduit 34. Originating also at the top of enclosure 10 is an exhaust conduit 38. The amount of exhaust which passes through exhaust conduit 38, and thereafter to the pollution control apparatus (not shown), is regulated by an exhaust damper 40.

Enclosure 10 defines an enclosed area and the amount of exhaust which is drawn through exhaust conduit 38 always approximtely equals the amount of fresh air which is drawn through fresh air inlet 32. Exhaust damper 40 and recirculation damper 36 are always driven oppositely, that is, as exhaust damper 40 is opened, so as to permit more air into exhaust conduit 38, recirculation damper 36 is closed, so as to permit less air into recirculation conduit 34.

Dampers 36 and 40 are pneumatically controlled in accordance with an electrical control signal generated by control assembly B. As is explained in detail below, during normal operation the control signal is generated by control assembly B in accordance with the web speed, as sensed by tachometer 16, and in accordance with the solvent concentration within enclosure 10, as sensed by a gas analyzer A. Gas analyzer A continuously samples the solvent concentration of the air within enclosure 10 through conduit 42. During calibration, when the control signal is a function of the web speed alone, gas analyzer A will first test a sample having zero solvent concentration and thereafter test a sample having a known solvent concentration (methane). Inputs from souces of each of these gases are provided and designated as 44 and 46 respectively. An input from a source of fuel (propane) for the flame in the gas analyzer is provided by means of conduit 48. Further, compressed air, used to draw exhaust from the flame cell, is provided through conduit 50.

Figure 2:
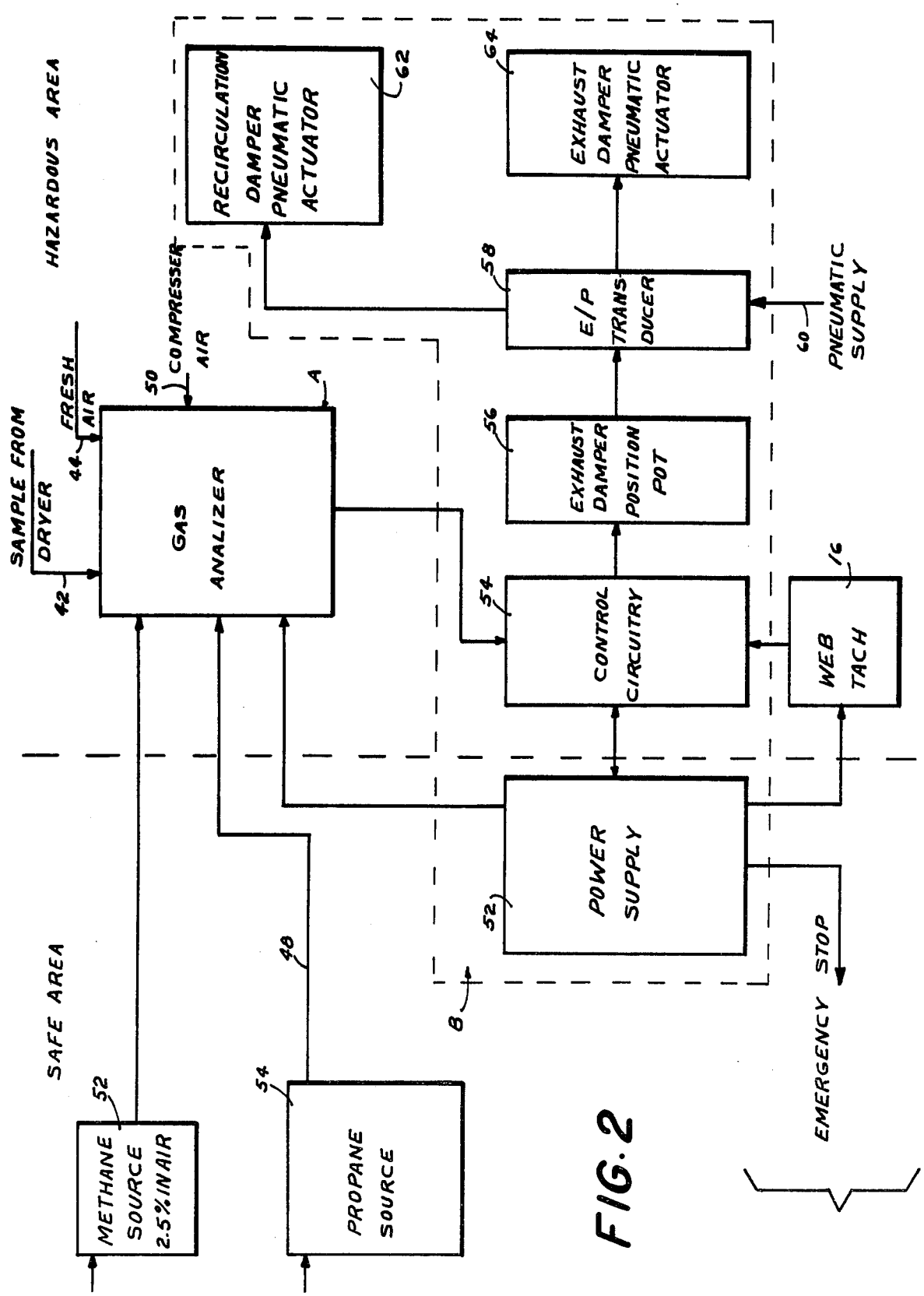
FIG. 2 is a schematic diagram of the LEL Control of the present invention.

With reference to FIG. 2, this figure shows gas analyzer A connected to enclosure 10 by means of conduit 42 to obtain a sample from the dryer, to a souce of zero concentration gas (air) by a means of conduit 44, to a source 52 of gas of a known solvent concentration (methane in air), to a fuel supply such as a propane source by means of conduit 48 and to a source of compressed air by means of conduit 50. Gas analyzer A is also connected to a power supply 52. Control assembly B, includes power supply 52 and control circuitry 54, described in detail below, which generates the damper control signal. The control signal, in accordance with the setting of an exhaust damper position potentiometer 56, drives an electric to pneumatic transducer 58, which is supplied with compressed air from a pneumatic supply, through a conduit 60. Transducer 58 drives recirculation damper pneumatic actuator 62 and exhaust damper pneumatic actuator 64. Inputs to control circuitry 54 include the output from the gas analyzer A, and the output from web tachometer 16, as well as the output from power supply 52.

Figure 3:
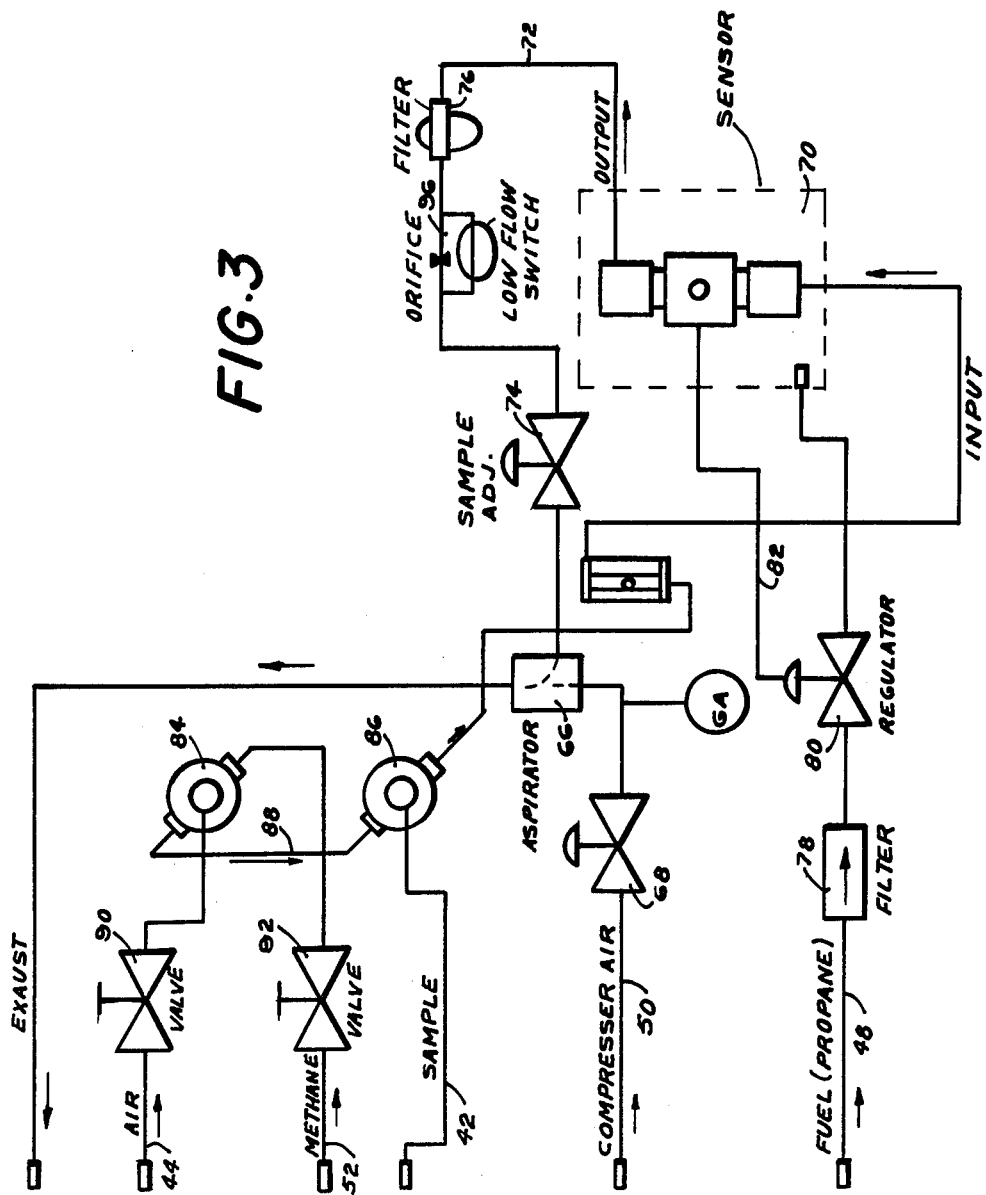
FIG. 3 is a flow-diagram of the gas analyzer which is associated with the control of the present invention.

FIG. 3 is a schematic diagram of the gas analyzer which forms a portion of the present invention. Gas analyzers are well known in the art in a variety of different forms. The analyzer described herein is model A1FFA Flammable Gas Detection System which is manufactured by Control Instruments Corporation, North Caldwell, N.J. However, different gas analyzers could be used for this purpose and the particular structure of the gas analyzer described herein should not be construed as a limitation on the present invention.

As shown in FIG. 3, compressed air (15 psi) enters the analyzer through conduit 50, which is connected to an aspirator 66 through a valve 68. The aspirator provides suction at the exhaust side of the flame cell 70 so as to draw exhaust fumes through exhaust conduit 72. A sample adjust valve 74 is connected in exhaust conduit 72 in order to regulate the flow through the cell. A filter 76 is provided in exhaust line 72 to protect aspirator 66.

Propane, which is utilized as fuel for the flame within cell 70, enters the system through conduit 48. Connected to conduit 48 is a fuel filter 78, a flow-control regulator 80 and a heated capillary (not shown). The flow-control regulator 80 is controlled by a feedback signal monitoring the flow (vacuum) in the flame cell, the feedback line being designated 82.

Three gas inputs are available to the flame cell for analysis: air (zero solvent concentration); methane (2.5% methane in air, a certified standard mixture) and sample (taken from the evaporation enclosure) through conduits 44, 52 and 42 respectively. Each of these sources is selected, one at a time, by means of two three-way solenoid valves 84 and 86. Valve 84 has conduits 44 and 52 as inputs (the former being normally opened and the latter being normally closed) and a connecting output conduit 88 which connects valve 84 to an input (normally closed) of valve 86. The other input (normally opened) of valve 86 is connected to conduit 42 and the output thereof is connected to the input side of the flame cell 70.

Located above the pilot flame in the flame cell 70 (but not shown on this drawing) is a resistance temperature detector, preferably comprised of platinum wire sensor which changes resistance with changes in temperatures. Since solvents have fuel value, as they pass through the pilot flame and oxidize, heat is released. The amount of heat released is proportional to the solvent concentration of the gas and this is sensed by the detector.

In order to calibrate the system of the present invention, zero solvent concentration gas (air) is first selected by means of the input solenoids 84 and 86 and analyzed. The output of the detector is used to balance a resistance bridge located in the control means, of which the detector forms a part, to 0% LEL setting. Then, the gas of known solvent concentration (methane) is selected and analyzed. This mixture corresponds to 64% LEL and the electronics are then balanced to this known input. Since 40% LEL is a maximum operating point, 64% represents a full scale calibration. After the electronics are calibrated, the sample input (from the evaporation enclosure) is again selected and analyzed. It is now possible for an accurate measure of the LEL concentration of the sample gas to be achieved.

Trim valves 90 and 92 are provided to balance the gas input flow rates in conduits 44 and 52 respectively. A low flow switch 96 is provided in conduit 72 and connected to the control assembly. If the flow rate becomes too low, the measuring accuracy of the analyzer will be comprimised and the output of the detector will be neglected through the actuation of low flow switch 96.

Figure 4:
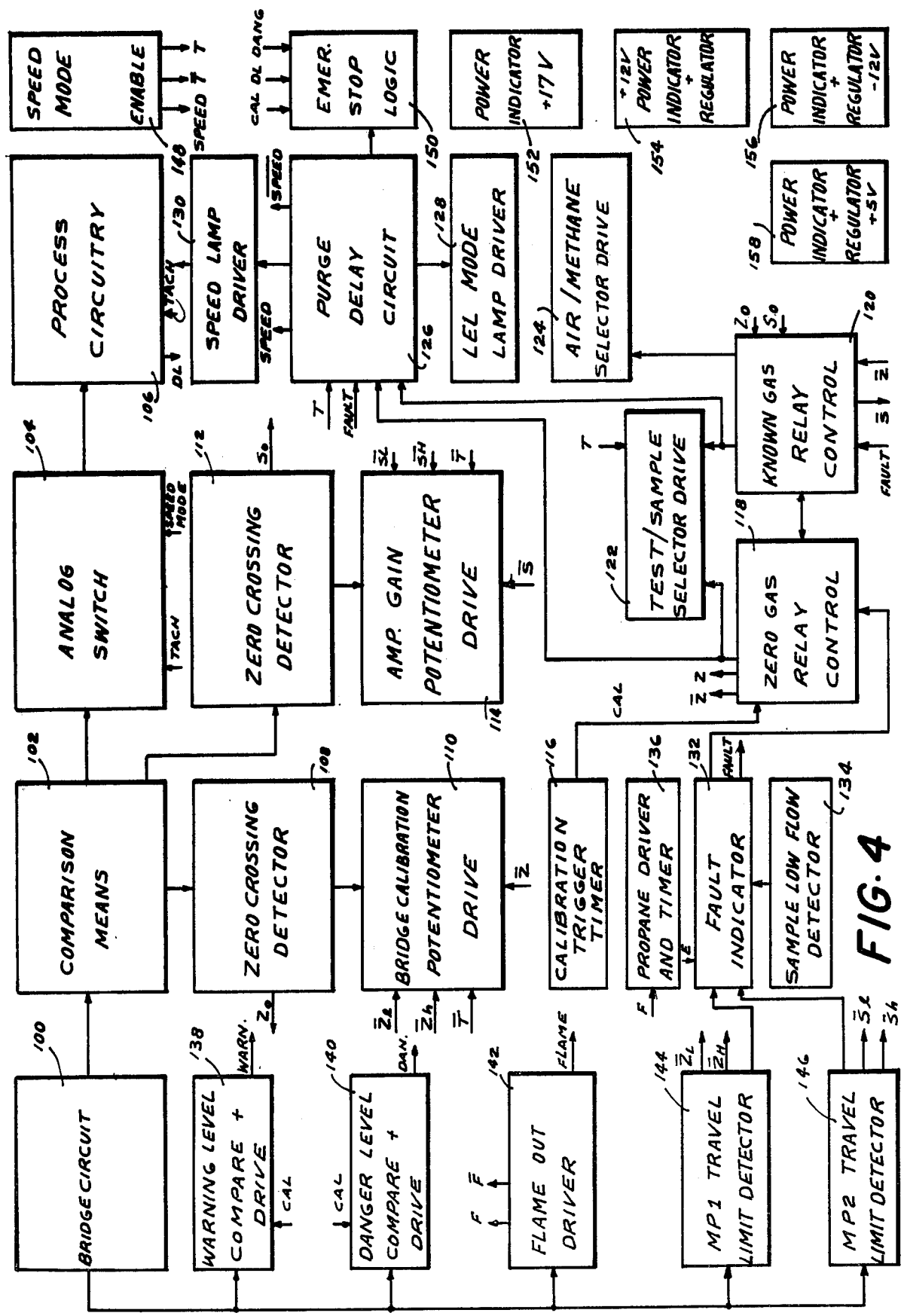
FIG. 4 is a detailed block diagram of the control circuit of the present invention.

FIG. 4 is a detailed block diagram of the control assembly of the present invention. In this drawing, block 100 represents the bridge circuit wherein the resistance of the detector, which is physically located in the gas analyzer, is measured. This block also includes an amplification means to amplify the bridge output and motorized potentiometers which calibrate the bridge and adjust the gain of the amplifier.

The output of block 100, which represents the measured LEL voltage, is connected to block 102 which includes voltage comparison means in the form of a differential amplifier. The differential amplifier makes three sets of comparisons: the first comparison is of the set LEL voltage to the measured LEL voltage of the sample gas; the second comparison is of zero volts to the LEL voltage of the zero solvent concentration gas for zero level calibration, and the third comparison is of a preset voltage to the LEL voltage of the known concentration gas for the full scale calibration. The output of the differential amplifier means is also utilized to operate the motorized potentiometers in order to calibrate the bridge and amplifier means of block 100.

The output of the comparison means of block 102 is connected to block 104. Block 104 contains electronics to partially process the amplifier output. Block 104 also contains switch means which are used to inhibit the output of the processing circuitry under certain conditions, such as during calibration, when the system is operating in the SPEED mode and the resultant control signal is based on the second control signal alone, which is derived from the output of tachometer 16.

The output of block 104 is connected to block 106 which contains further signal processing circuitry. Block 106 receives the web speed signal from tachometer 16, the web speed signal being combined in block 106 with the output of block 104. Block 106 also contains a level detector to signal an emergency stop if the feedback signal from the exhaust damper is invalidated. The output of block 106 is the damper control signal and is connected to an electric to pneumatic transducer 58 (shown in FIG. 2 but not shown in FIG. 4) which drives an exhaust damper position actuator which in turn drives the exhaust damper and the recirculation damper.

It can thus be seen that during normal operation (LEL mode), the solvent concentration of the gas sample from the evaporation enclosure is measured and amplified in block 100 and compared to a set LEL voltage by means of a differential amplifier in block 102. The output of block 102 is partially processed in block 104 and further processed in block 106 where it is combined with the signal based on the web speed. The output of block 106 drives an electric to pneumatic transducer which in turn positions the dampers. In this matter, the exhaust damper is positioned in accordance with the solvent concentration level of the sample from the enclosure and the web speed.

During calibration or manual actuation of the SPEED mode, the switch means located in block 104 inhibits the voltage output of the block 102 and the resultant control signal is proportional to the input from web tachometer 16 alone. When calibration is initiated, the SPEED mode is automatically selected and the exhaust damper is no longer poistioned with respect to the output from the bridge circuit but is instead positioned only in accordance the second control signal based on the output from web tachometer 16, which is proportional to the web speed. This permits the bridge in block 100 to be calibrated without adversely affecting the damper position.

Calibration takes place in two phases. First, a calibration at the 0% solvent concentration level takes place. By means of a relay, a switch in block 102 is actuated so as to cause the differential amplifier therein to make a comparison of zero volts to the amplified bridge output, when the zero solvent concentration level gas (air) is analyzed. Block 110, which is connected to the output of the differential amplifier in block 102 by a relay, during this phase of calibration, contains the bridge calibration potentiometer drive circuitry which drives potentiometer MP1 in order to calibrate the bridge at the 0% LEL setting. Block 108, also connected to receive the output from block 102 during this phase of calibration, contains a zero crossing detector whose output $Z_o$ prevents motorized potentiometer MP1 from driving past the calibration point.

After the 0% solvent concentration level setting has been calibrated, the gas of known solvent concentration is a analyzed, the output of the amplifier compared to the full scale reference voltage and the comparison means output is fed to block 114 by a relay. Block 114, which contains the amplifier gain potentiometer drive circuitry, will calibrate the gain of the bridge output amplifier, located in block 100, to the full scale setting. Block 112, which contains a zero crossing detector, also receives the output of the comparison means during this phase of calibration and generates a signal $S_o$ to prevent potentiometer MP2 from driving past the calibration point.

The calibration cycle is initiated periodically by block 116 which triggers the cycle. The output of block 116 is transferred to blcok 118 which includes the 0% solvent concentration gas relay control. One of the outputs of block 118 is connected to block 122 which controls solenoid valve 86 in the gas analyzer such that the B 0% solvent level concentration gas (air) is analyzed. Another output Z of block 118 is connected to the bridge calibration potentiometer circuitry in block 110 to permit actuation thereof.

After the 0% concentration level phase of calibration is completed, block 118 generates an output to the known solvent concentration gas relay circuitry block 120. Block 120 generates an output to the air/methane selector drive circuit in block 124 to accuate the solenoid valve 84 in the gas analyzer to permit the known solvent concentration gas (methane) to fill the flame cell. Another output of block 120 $\overline{S}$ is connected to the amplifier gain potentiometer drive circuit in block 114 to permit actuation thereof during this phase of calibration.

After the full scale phase of calibration is completed, signaling the end of the calibration cycle, block 120 generates an output to block 122 to return solenoid 86 to its original state wherein the sample from the enclosure 10 is the input to the flame cell. A purge delay circuit in block 126 also receives the output of block 120 and causes a one-minute delay during which the flame cell of the gas analyzer is purged. After this delay, the system automatically returns to its normal or LEL mode and calibration is completed. Outputs of block 126 control the LEL mode lamp driver circuit in block 128 and the SPEED lamp driver circuit in block 130. Outputs of block 126 are also the SPEED and $\overline{SPEED}$ signals.

Block 132 comprises circuitry which establishes the logic for FAULT conditions. One of the inputs for block 132 is generated in block 134 which contains a sample low flow detector which is operably connected to low flow switch 96 (FIG. 3) in the gas analyzer. Other inputs to block 132 come from blocks 144 and 146, which contain the potentiometer limit detectors.

Block 136 controls the propane supply to the gas analyzer. Block 138 and 140 each receive an output of the bridge circuit of block 100. Block 138 contains a comparator which compares the output of the bridge circuit to a preset voltage and, under the proper conditions, drives a WARNING lamp. Block 140 contains a comparator which compares the output of the bridge circuit to a second preset voltage, and under the appropriate conditions, drives a DANGER lamp. Block 142, also connected to the bridge circuit in block 100, contains a voltage comparator which, in the event that the flame has gone out in the gas analyzer, will drive a FLAME OUT lamp.

Variable resistors in blocks 144 and 146 are connected respectively to the bridge calibration potentiometer MP1 and amplifier gain potentiometer MP2 and also receive an output from block 100. Blocks 144 and 146 act as limit detectors for each of the potentiometers.

Block 148 is connected to a manually actuated mode selector switch on the front panel of the control assembly and generates the appropriate signals to enable manual actuation of the SPEED or TEST modes. Block 150 receives the output of block 126 and is utilized to initiate the "emergency stop" signal which will stop the press under a danger condition. Block 152 represents the +17 volt power indicator. Blocks 154, 156 and 158 constitute power indicators and regulators for +12 volts −12 volts and +5 volts, respectively.

Figure 5:
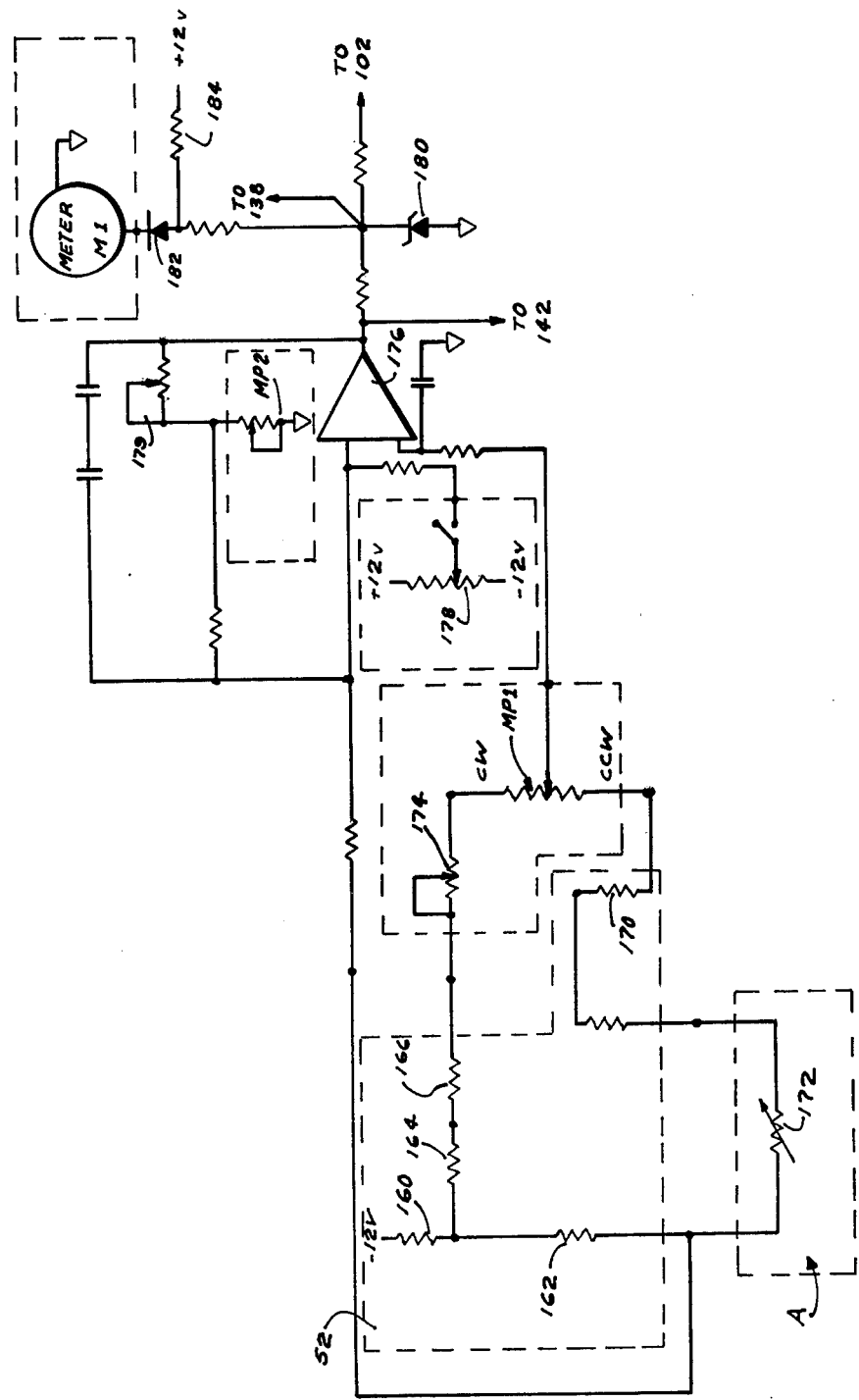
FIG. 5 is a schematic diagram of the resistnce bridge and signal amplification means of the present invention.

FIG. 5 is a detailed schematic diagram of block 100. As shown on this diagram, the input bridge circuit is formed of resistors 160, 162, 164, 168 and 170 located in power supply 52, a resistance temperature detector 172, located within gas analyzer A, the bridge calibration motorized potentiometer MP1 and a variable resistor 174. The resistance temperature detector 172 is preferably a platinum wire sensor whose resistance changes as a function of temperature. Motorized potentiometer MP1 is driven, as explained in detail below, in order to calibrate the bridge to the 0% LEL setting when the zero solvent concentration gas is analyzed, during the first phase of calibration. Variable resistor 174 is utilized to trim the bridge initially.

Figure 6:
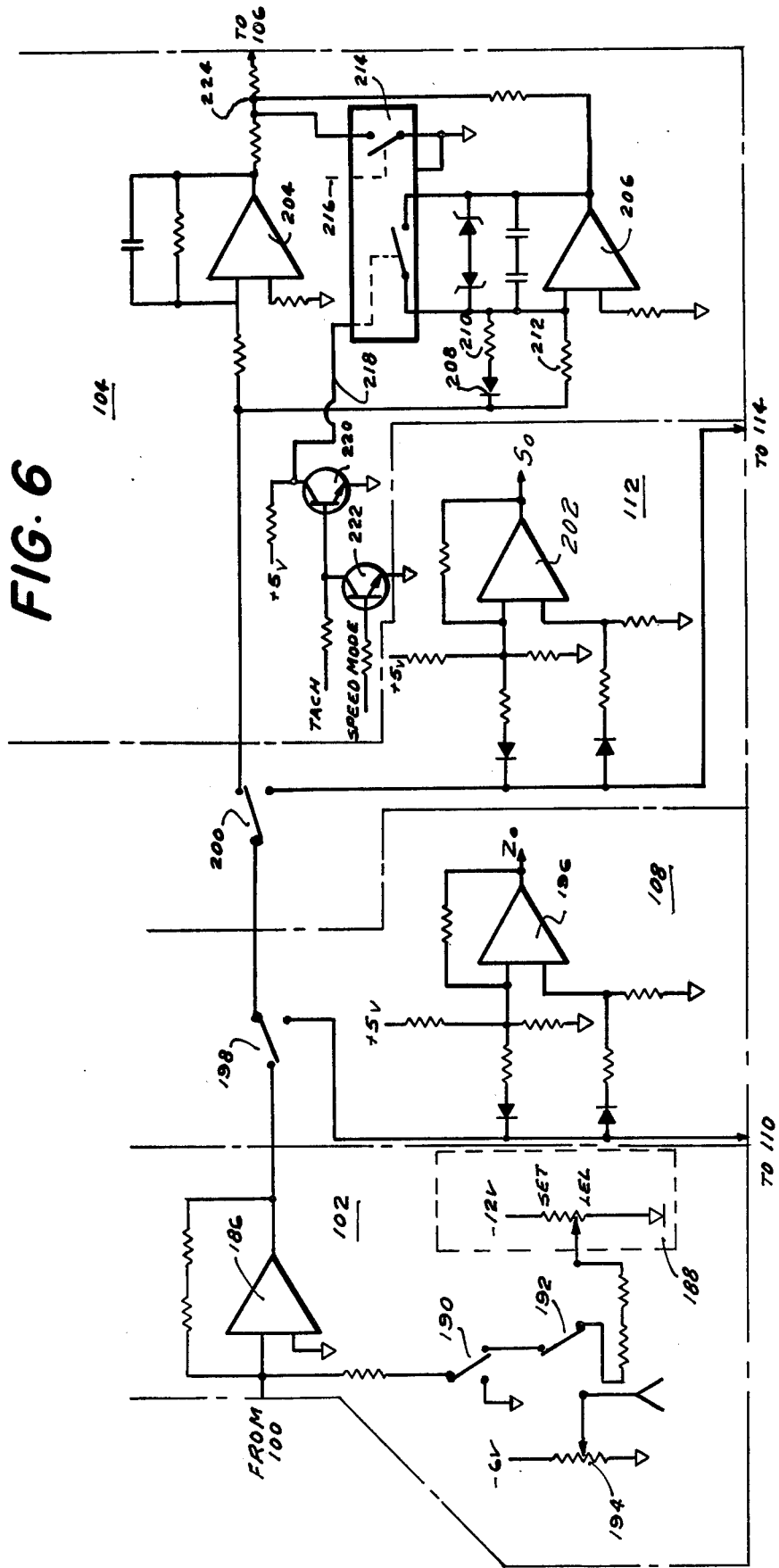
FIG. 6 is a schematic representation of the comparison means, analog switch circuit and the zero crossing detector circuits of the present invention.

The output of the bridge forms the input for an amplifier 176. A variable resistor 178 is provided for manual switching into the circuit. Amplifier 176 is connected to a feedback circuit which is used to adjust the amplifier's gain during the full scale phase of calibration. This gain adjustment is accomplished by means of the amplifier gain motorized potentiometer MP2, which is driven in the manner disclosed in detail below. A variable resistor 179 is used to trim the range of the amplifier. The output of amplifier 176 is limited by a diode 180. A meter M1 is connected to amplifier 176 such that the output thereof can be monitored. Meter M1 is protected for excessive negative voltage by diode 182 and resistor 184. One output of amplifier 176 is fed to block 102 which is schematically shown in FIG. 6.

Block 102 includes a differential amplifier 186 which is connected so that its output will go to zero when both inputs are equal. Differential amplifier 186 makes, by relay control, three comparisons. The first is a comparison of the set LEL voltage, derived from variable resistor 188, to the measured LEL voltage from the bridge circuit of block 100. If the output of the bridge circuit is higher or lower than the set LEL voltage, the appropiate signal will be generated by differential amplifier 186 so as position the damper to bring the solvent concentration within the evaporation enclosure back to the desired level. This takes place when relays 190 and 192 are in the positions shown in FIG. 6.

During calibration and more specifically during the first phase thereof, relay 190 is actuated by block 118 to its alternate position such that the amplifier 186 is connected to ground. The zero solvent concentration gas is analyzed and the output of block 100 is compared to ground thereby permitting the bridge calibration motorized potentiometer MP1 to set the bridge to the appropriate 0% LEL setting, as described below. During the second phase of calibration, relay 190 returns to its original position and relay 192 is actuated by block 120 to its alternate position. This configuration of relays 190 and 192 causes amplifier 186 to be connected to a variable resistor 194. Resistor 194 generates the known solvent concentration reference voltage to permit full scale calibration. This voltage is compared to the output of block 100 when the known solvent concentration gas is analyzed and the amplifier gain motorized potentiometer MP2 is appropriately actuated for full scale calibration as described below. The output of differential amplifier 186 is connected to block 108.

Block 108 contains an IC 196 (LM1414N available from National Semiconductor, Inc.) which acts as a zero crossing detector. The input to IC 196 is connected to the output of differential amplifier 186 by means of relay 198 also actuated by block 118 to change the relay from the position shown to the alternate position during the first phase of calibration. The output of zero crossing detector 196, designated as $Z_O$, is used to stop the bridge calibration motorized potentiometer MP1 from driving past the calibration point. The other output from block 108, which is the LEL voltage from amplifier 186, is connected to the bridge calibration potentiometer drive circuit in block 110.

During the second phase of calibration, relay 198 returns to its original position and relay 200 is actuated by block 120 to its alternate position, thereby connecting the output of amplifier 186 to IC 202 (LM1414N available from National Semiconductor, Inc.) which acts as a zero crossing detector for full scale calibration. The output of IC 202, designated as $S_O$, is used to stop the amplifier gain motorized potentiometer MP2 from driving past the calibration point. Relay 200 is also connected to the amplifier gain potentiometer drive circuit in block 114.

When relays 198 and 200 are in the positions shown, the output of amplifier 186 is connected to the input of IC 204 (5B7741393 available from Fairchild) in block 104, which functions as a proportional attenuator of the amplifier output and also as a derivative amplifier responding to rapid changes at the input. The output from differential amplifier 186 also forms an input to IC 206 (5B7741393 availabe from Fairchild) in block 104 which functions as an integrator for the output of the differential amplifier. The time constants for integrator 206 are set by diode 208 and resistors 210 and 212, such that the time constants are faster for an increasing LEL voltage than for a decreasing LEL voltage.

Also included with block 104 is an IC 214 (AHO134D available from National Semiconductors, Inc.) which acts as an analog switch. Analog switch 214 has two inputs 216 and 218. Inputs 216 is connected to receive the SPEED mode signal from block 126. When this signal is present, analog switch 214 inhibits the output of IC 204. Input 218 of switch 214 is connected to the collector of a transistor 220, the base of which is connected to the collector of a transistor 222. The base of transistor 220 is connected to receive the signal from tachometer 16 and if this signal is not present, i.e., the press is not operational, transistor 220 will turn on, grounding input 218 and therby inhibiting the integral output of IC 206. Transistor 222, the base of which is connected to receive the SPEED mode signal, will also ground the base of transistor 220 in the presence of this signal, therby causing analog switch 214 to inhibit the integral output of IC 206. Thus, while the system is operating in the SPEED mode, such as during calibration, or if the SPEED mode is manually enabled, the outputs of IC's 204 and 206 are inhibited. The combined outputs of 204 and 206, when same are operative, are summed at diode 224, which forms the output of block 104 and which is connected to the input of block 106.

Figure 7:
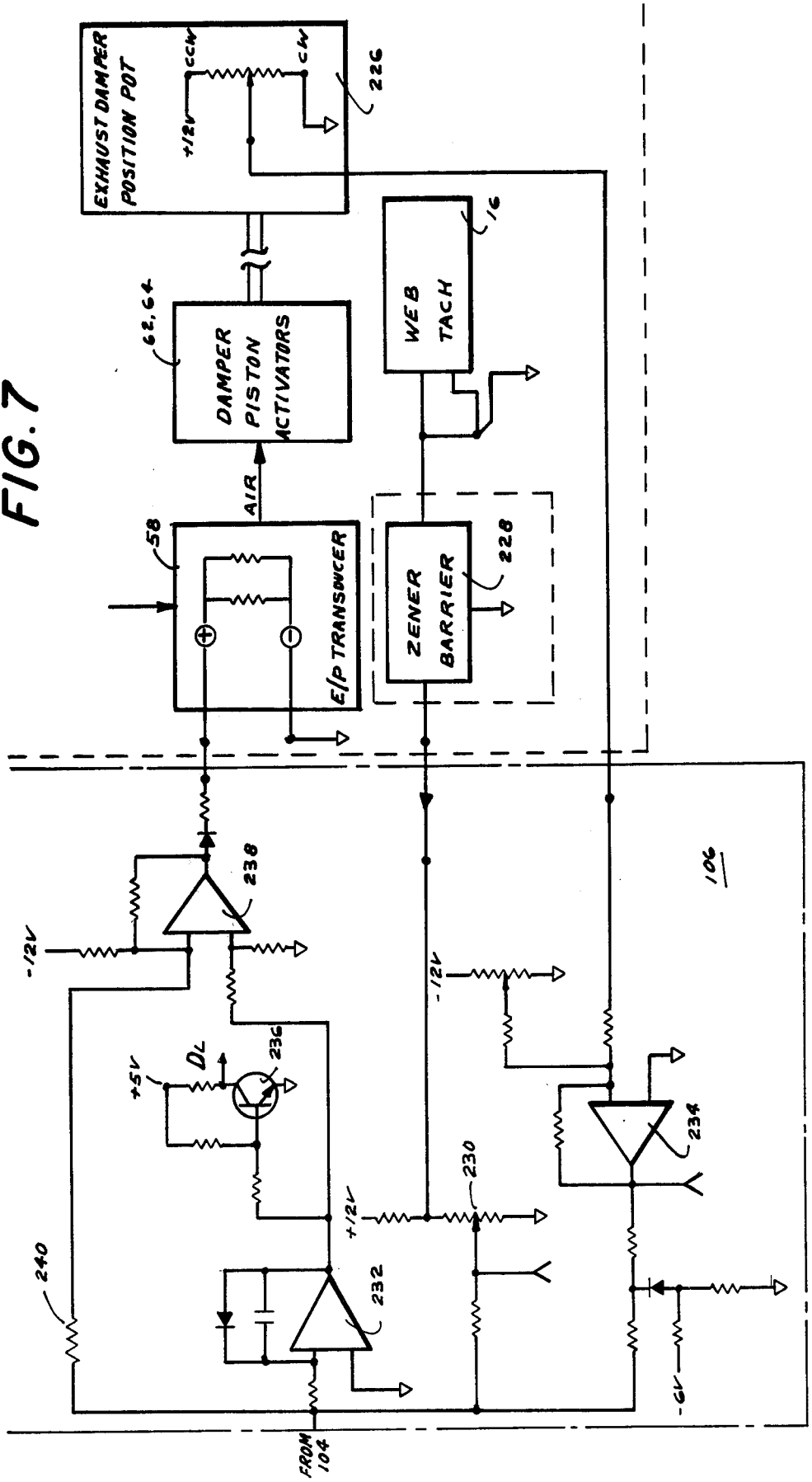
FIG. 7 is a schematic diagram of the signal processing circuitry and a block diagram of the damper control devices of the present invention.

As seen in FIG. 7, block 106 has inputs from block 104, representing the partially processed signal proportional to the detected solvent concentration level, from web tachometer 16 and from an exhaust damper position potentiometer 226. The output of web tachometer 16 passes through a Zener barrier 228 and then through a variable resistor 230 prior to forming an input to an IC 232 (5B7741393 available from Fairchild) which acts as an integrator. The output of the exhaust damper position potentiometer 226 is connected to one of the inputs to an IC 234 (5B7741393 available from Fairchild), which functions as an inverting amplifier with an adjustable offset for exhaust damper position potentiometer compensation. The output IC 234 is then modified to establish two ranges of linear proportionality.

The output of IC 232 is connected to the base of a transistor 236, which is used as a level detector to generate signal $D_L$, if the feedback signal from the exhaust damper is invalidated. The signal $D_L$ is generated at the collector of transistor 236. The output of IC 232 is also connected to one of the inputs of IC 238 (5B7741393 available from Fairchild). The other input IC 238 is connected, by means of a resistor 240, to the output of IC 232. IC 238 functions as proportional attenuator and as a level shifter to properly range the output signal to the electric to pneumatic transducer 58. Transducer 58 converts the electrical signal output of IC 238 into a pneumatic drive which is connected to damper position actuators 62 and 64 so as to position the exhaust and recirculation dampers.

Figure 8:
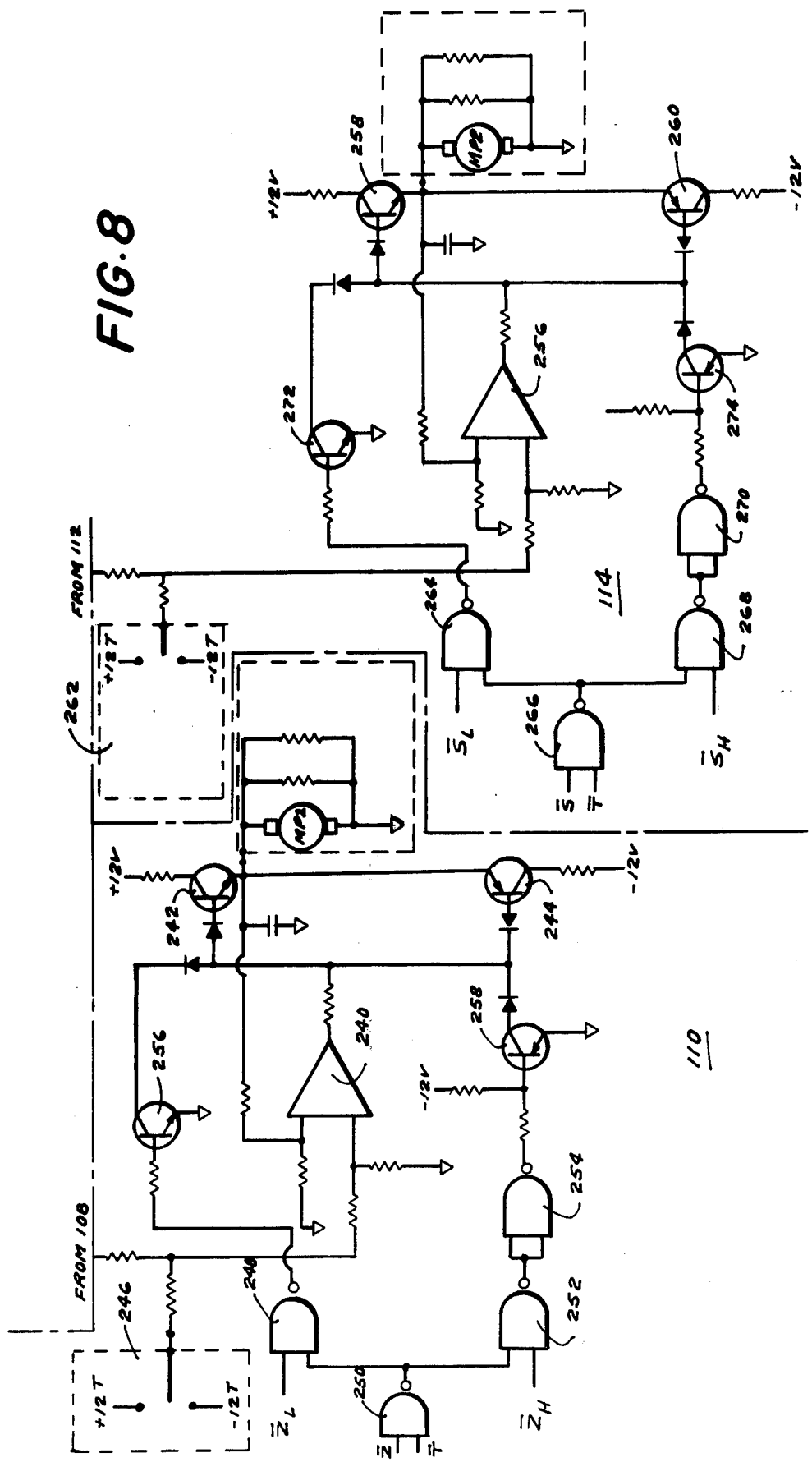
FIG. 8 is a schematic diagram of the drive circuits for the motorized potentiometers used to calibrate the system of the present invention.

FIG. 8 contains schematic diagrams for block 110 and block 114, which are the bridge calibration potentiometer drive circuit and amplifier gain potentiometer drive circuit, respectively. During the first phase of calibration, the output from block 108, which represents the bridge circuit amplifier output when the zero solvent concentration gas (air) is analyzed, is connected to one of the inputs of an IC 240 (5B7741393 available from Fairchild). IC 240 functions as non-inverting amplifier with motorized potentiometer MP1 providing a feedback signal to the other input thereof. Amplifier 240 serves to bias either transistor 242, connected to a +12 volt source, or transistor 244, connected to a −12 volt source, to drive motorized potentiometer MP1 in the proper direction, that is, clockwise or counter-clockwise. A switch 246 is provided on the front panel of the control assembly in order to manually actuate the motorized potentiometer. Logic gates 248, 250, 252 and 254 are utilized to gate the circuit for operation. All of the inputs to these logic gates must be high (logic one) in order to turn off transistors 256 and 258 so as to permit MP1 to be driven. One input of gate 248 is a signal $\overline{Z}_L$ which is generated by MP1 travel limit detector of block 144. One input to gate 252 is a signal $\overline{Z}_H$ which is also generated by MP1 travel limit detector of block 144. Gate 250 receives logic signals $\overline{Z}$ and $\overline{T}$, which are generated by block 118 and block 148, respectively. The other inputs to gates 248 and 252 receive the output of gate 250.

Block 114 has a structure quite similar to block 110. The output from block 112, which is representative of the output of the bridge circuit amplifier when the gas of known solvent concentration is analyzed, serves as one of the inputs of IC 256 (5B7741393 available from Fairchild). IC 256 serves as a non-inverting amplifier with motorized potentiometer MP2 providing a feedback signal. Amplifier 256 biases transistor 258, connected to a +12 volt source, or transistor 260, connected to a −12 volt source, in order to drive motorized potentiometer MP2 in the proper direction. A switch 262 is provided on the front panel of the control assembly in order to manually regulate the position of motorized potentiometer MP2. Logic gates 264, 266, 268 and 270 are provided and the input to each must be high or logic one, in order to turn off transistors 272 and 274 to permit driving of the potentiometer. The logic input to gate 264 is $\overline{S}_L$, one output from block 146. The input to gate 268 is signal $\overline{S}_H$ which is another output of block 146. The inputs to gate 266 are $\overline{S}$ and $\overline{T}$, generated by block 120 and block 148, respectively.

Figure 9:
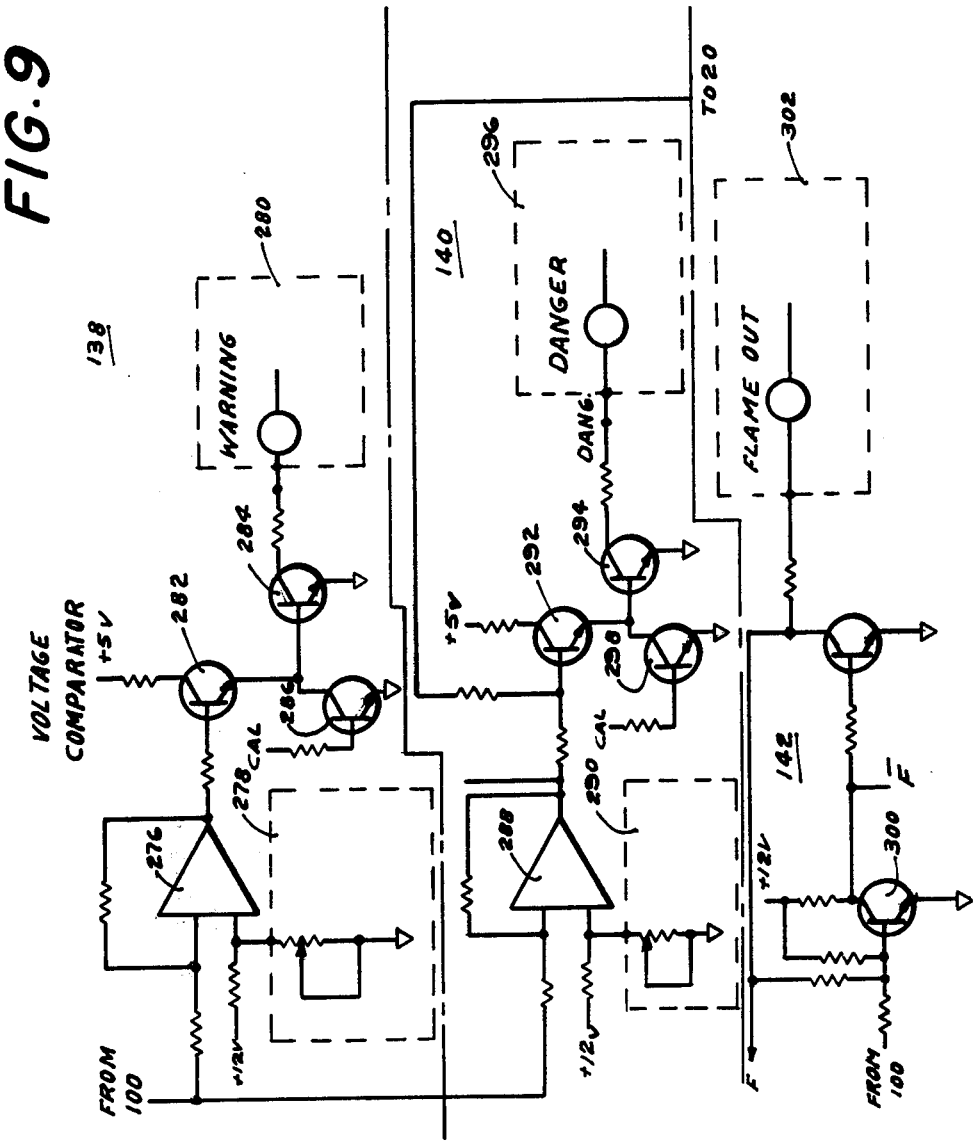
FIG. 9 is a schematic diagram of the driver circuits for the warning, danger and flame out lamps of the present invention.

FIG. 9 contains schematic diagrams of the warning level comparator and driver circuit of block 138, danger level comparator and drive circuit of block 140 and "flame out" driver circuit of block 142. The input to blocks 138 and 140 is connected to block 100 and more particularly, to the output of amplifier 176 where this output is connected to the mode between diodes 180 and 182. Thus, the input to blocks 138 and 140 represents the amplified bridge circuit output. Block 138 contains an IC 276 (LM1414N available from National Semiconductors, Inc.) which is utilized as a voltage comparator. The comparison voltage is set by a variable resistor 278, which represents the warning level, that is, the solvent concentration level above which the WARNING lamp 280 is to be energized. The output of the voltage comparator drives WARNING lamp 280 through transistor 282 and 284. The base of transistor 286 is connected to receive the CAL signal output of block 116. The presence of the CAL signal causes transistor 286 to turn on, thereby grounding the base of transistor 284 and preventing the actuation of WARNING lamp 280 during the calibration cycle.

Block 140 is structurally similar to block 138. This block contains an IC 288 (LM1414N available from National Semiconductor, Inc.), one input of which is connected to receive the amplified bridge output signal. The other input of IC 288 is connected to a variable resistor 290, which sets the danger level voltage. IC 288 acts as a voltage comparator and when a voltage above the level set by resistor 290 is sensed, transistors 292 and 294 are turned on thereby generating the DANG signal and actuating DANGER lamp 296. The base of the transistor 298 is connected to receive the CAL signal output from block 116 thereby inhibiting the actuation of DANGER lamp 296 during the calibration cycle.

The input of block 142 is connected to the output of bridge circuit in block 100 at the output of amplifier 176. This input is connected to the base of a transistor 300, which is utilized as a voltage level detector. When an output signal from bridge circuit 100 is detected to be under a certain magnitude, the FLAME OUT lamp 302 is turned on to indicate that the flame has gone out in the gas analyzer. Logic signal $\overline{F}$ is also generated by this circuit representing the flame out condition.

Figure 10:
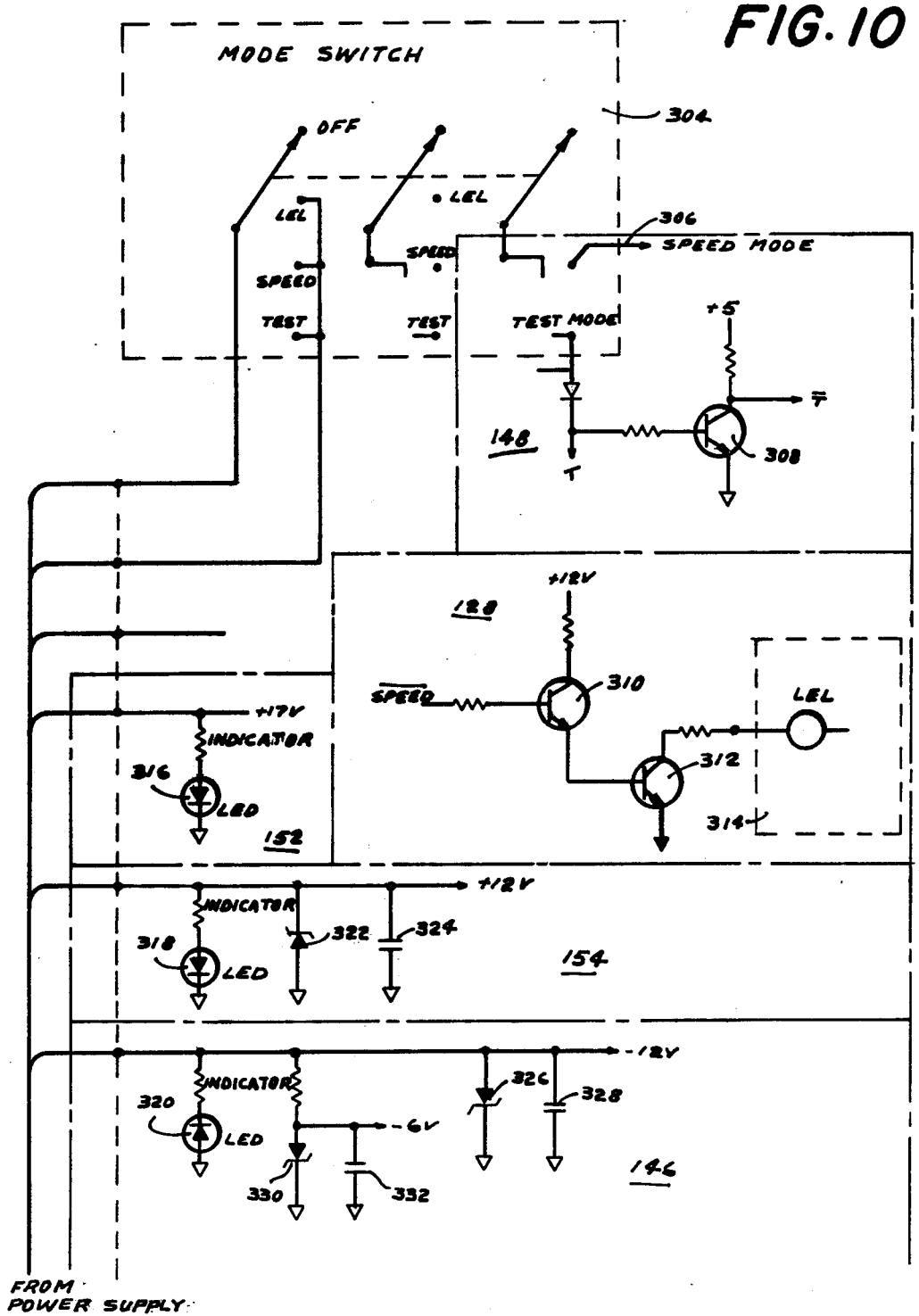
FIG. 10 is a schematic diagram of the mode selector switch, speed mode enable circuit, LEL lamp driver circuit and power indicator lamp driver circuits of the present invention.

FIG. 10 shows a schematic representation of the mode switch 304, SPEED mode enable circuit of block 148, LEL mode lamp driver circuit of block 128, power indicator circuit of block 152, power circuit and regulator circuit of block 154 and power indicator and regulator circuit of block 156. Mode switch 304 has four positions, off, LEL mode, SPEED mode and TEST mode. FIG. 10 shows mode switch 304 in the off position. When switch 304 is in the speed mode position, the SPEED signal is generated as an output of block 148 at mode 306. When mode switch 304 is in the test mode position, block 148 generates two complimentary logic signals T and $\overline{T}$. The output upon which $\overline{T}$ is generated is connected to the collector of a transistor 308, that base of which is connected to the mode switch 304.

Block 128 contains the LEL mode lamp driver circuit. This circuit consists of two transistors 310 and 312. The base of transistor 310 receives the complement of the SPEED signal and when this signal is present, that is, when the system is not in the speed mode, LEL lamp 314 is energized.

Blocks 152, 154 and 146 each contain a light emitting diode 316, 218 and 320, respectively, which act as an indicator to show the presence of +17 volt, +12 volt and −12 volt power voltages respectively. Block 154 also contains a voltage regulation circuit comprised of diode 322 and capacitor 324. Likewise, block 146 contains a diode 326 and a capacitor 328 which act to regulate tne −12 volt output and diodes 330 and 332 which act to regulate the −6 volt output.

Figure 11:
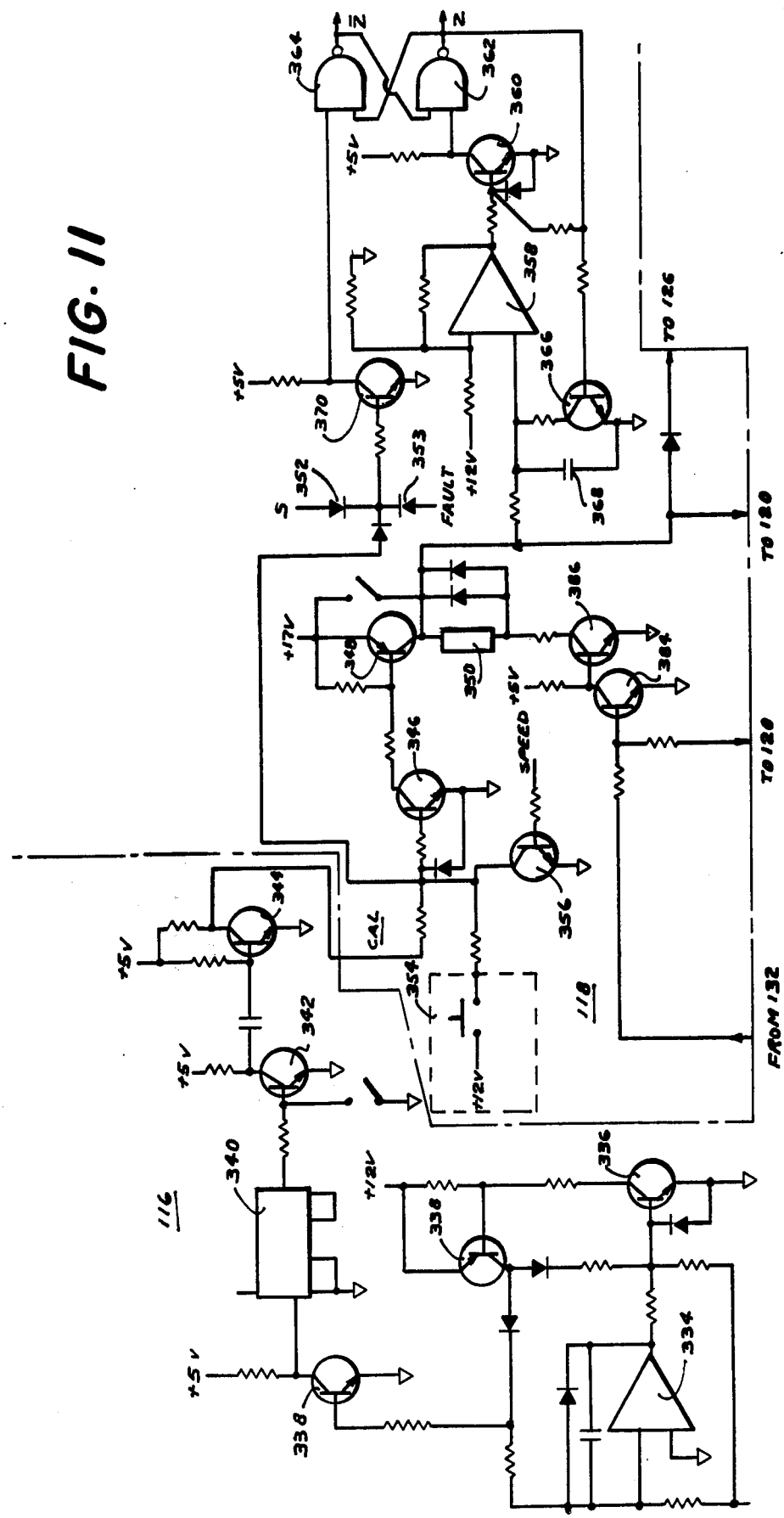
FIG. 11 is a schematic diagram of the calibration trigger circuit and the zero solvent concentration level gas relay control circuit of the present invention.

FIG. 11 shows a schematic diagram of the calibration trigger circuit of block 116 and zero solvent concentration gas relay control circuit of block 118. Block 116 contains an IC 334 (LM1414N available from National Semiconductor, Inc.) and transistors 336 and 388, which along with associated components function as an astable multi-vibrator with a frequency of about 22 minutes. The output of the multi-vibrator is connected to the base of transistor 388 which triggers an IC 340 (SN74L93 availabe from Texas Instruments) which functions as a divide by 16 counter, thereby generating an output approximately every six hours to initial calibration. The calibration trigger signal CAL apperars at the collector of transistor 344.

The calibration trigger signal CAL forms the input to the zero solvent concentration gas relay control circuit of block 118. Block 118 is the first stage to respond to the calibration trigger. The CAL signal input is fed to the base of a transistor 346 which in turn operates transistor 348 and thus, relay 350 which in turn operates switches 190 and 198 (see FIG. 6) to commence the first phase of calibration. This will occur as long as the FAULT signal (from block 132) is not present as an input to transistor 384. A manual calibration initiation switch 354 is provided and when actuated will trigger the calibration cycle as long as the SPEED mode signal is present at the base of transistor 356.

IC 358 (5B7741393 available from Fairchild), one input of which is connected to the output circuit of transistor 348, acts as an integrator. When the output of IC 358 reaches a positive voltage, transistor 360 turns on, latching the bistable circuit formed of gates 362 and 364 to generate the Z and $\overline{Z}$ logic signals, respectively, the output of gate 362 is connected to the base of a transistor 366. Timing capacitor 368, connected across the output circuit of transistor 366, discharges through transistor 366 to reset the bistable circuit. Transistor 370, whose base is connected to receive the S signal, through diode 352 and the FAULT signal through diode 353, also acts as a reset for the bistable circuit comprised of gate 362 and 364. The S signal output from block 120 represents the actuation of the second phase of calibration. When the bistable circuit resets, relay 350 is de-energized and the second phase of the calibration cycle is initiated. It should be appreciated that the output of gate 364, $\overline{Z}$ is connected as an input to bridge calibration potentiometer drive circuit in block 110 and it is during the time when the circuit is latched that the potentiometer MP1 will be driven.

Figure 12:
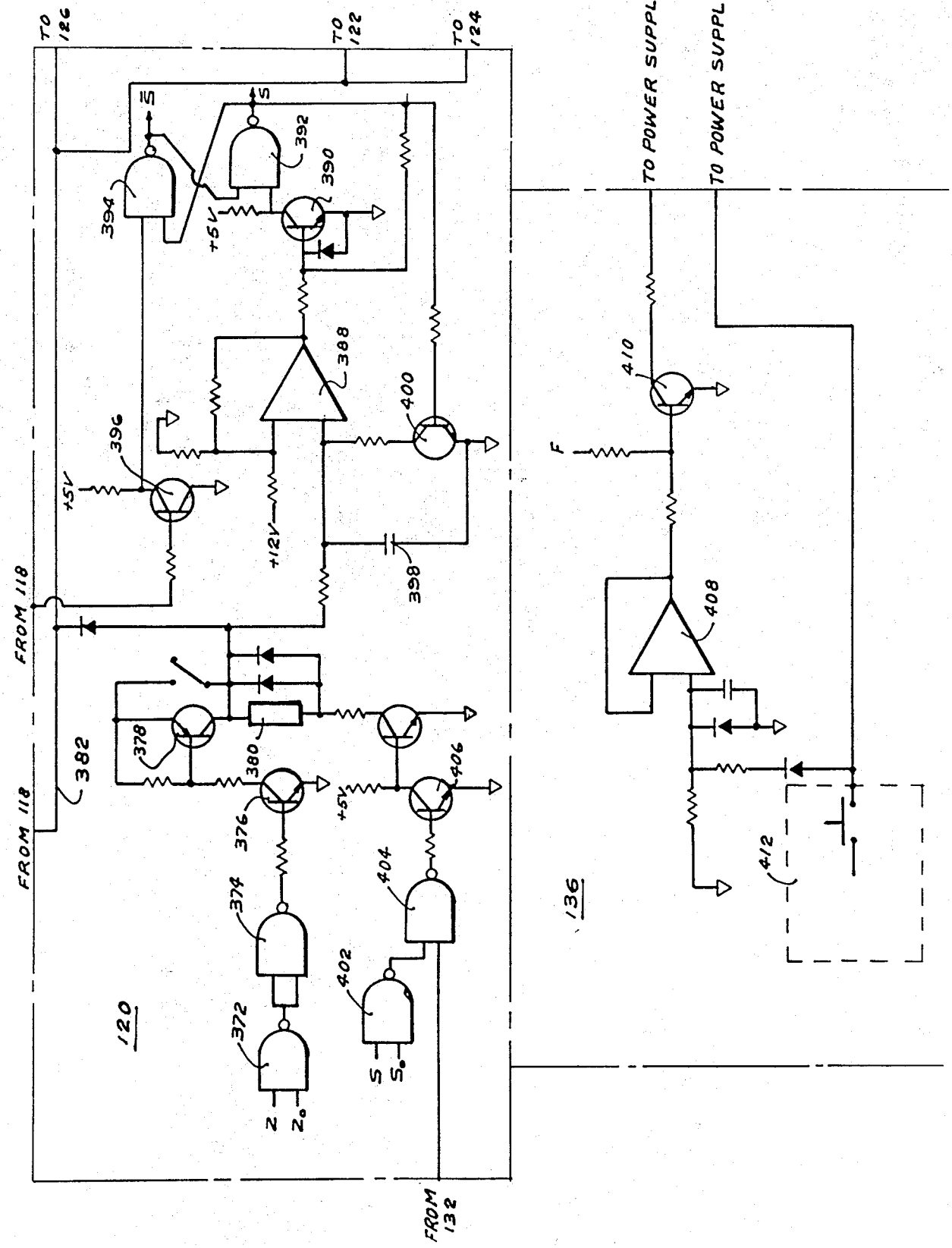
FIG. 12 is a schematic diagram of the known solvent concentration level gas relay control circuit and the propane driver and timer circuit of the present invention.

FIG. 12 shows schematic diagrams of the known solvent concentration gas relay control circuit of block 120 and propane driver and time circuit of block 136. When the signal ouput Z of gate 362 (FIG. 11) is high or logic one, the bridge calibration potentiometer MP1 will be driven until the output $Z_O$ of the zero crossing detector circuit of block 108 goes high or logic one. Signals Z and $Z_O$ constitute the inputs to a gate 372 hich in turn feeds gate 374. The output of gate 374 is connected to the base of transistor 376. When actuated, transistor 376 turns on transistor 378 which in turn energizes relay 380 to actuate switches 192 and 200 (FIG. 6) connecting the system for full scale calibration. This occurs as long as the FAULT signal (from block 132) is not present on line 382. Turning on a relay 380 causes the generation of the logic S signal, this causing relay 350 (FIG. 11) to be deactuated.

IC 388 (5B7741393 available from Fairchild), one input of which is connected to the output circuit of transistor 378, acts as an integrator. When the output of IC 388 reaches a positive voltage, trnsistor 390 is turned on thereby latching the bistable circuit comprised of gates 392 and 394, to generate the S and $\overline{S}$ logic signals. Transistor 396 acts as a reset for this latch, the base thereof being connected to an output of block 118.

Timing capacitor 398 discharges through the output circuit of transistor 400 when the S logic signal, connected to the base thereof, is high or in the logic one state to reset the bistable circuit. The S signal provides one of the inputs to gate 402. The other input to gate 402 is the $S_O$ signal, generated by zero crossing detector circuit of block 112. The output of gate 402 provides one of the inputs for gate 404, the other being the FAULT signal received from block 132. When signal S is high or logic one, the amplifier gain potentiometer drive circuit of block 114, one of whose inputs is the S signal, will drive motorized potentiometer MP2 until the output $S_O$ of the zero crossing detector circuit of block 112 goes high or logic one. When this occurs, transistor 406 causes relay 380 to turn off, thereby causing switches 192 and 200 (FIG. 6) to return to their original positions.

Also shown in FIG. 12 is a schematic diagram of the propane driver and timer circuit of block 136. This circuit comprises an IC 408 (5B7741393 available from Fairchild) which operates as an integrator, holding transistor 410 in its "on" condition for 14 minutes after ignition switch 412 is depressed. The base of transistor 410 is also connected to receive the complement of the FLAME OUT signal $\overline{F}$ and transistor 410 will remain on as long as this signal is present. Transistor 410 controls the propane supply to the gas analyzer.

Figure 13:
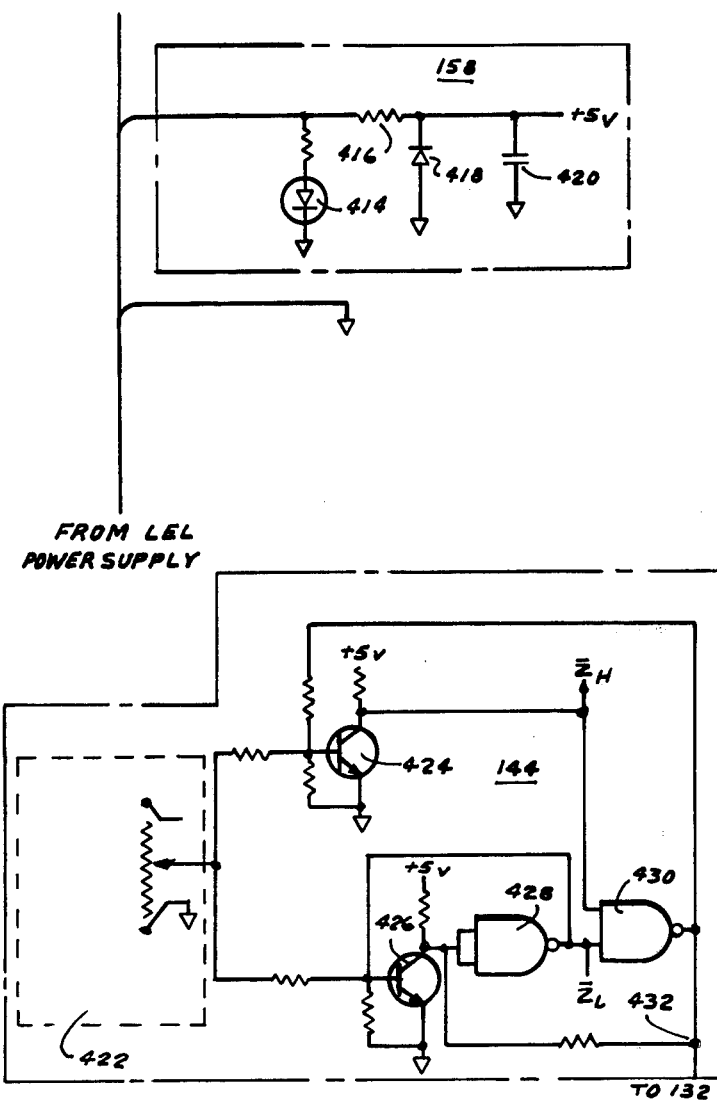
FIG. 13 is a schematic diagram of a power lamp indicator driver circuit and of the first potentiometer travel limit detector of the present invention.

FIG. 13 shows a schematic diagram of the power indicator and regulator circuit of block 158 and a schematic diagram of the MP1 travel limit detector circuit of block 144. Block 158 is connected to the power supply and contains a light emitting diode 414 which indicates the presence of the +5 voltage from the power supply. Voltage regulation is accomplished by means of resistor 416, diode 418 and capacitor 420.

Block 144 is the MP1 travel limit detector circuit. Potentiometer 422 is mechanically connected to the shaft of motorized potentiometer MP1. Transistors 424 and 426 and gates 428 and 430 form an electric limit on the travel of motorized potentiometer MPL with logic outputs $\overline{Z}_L$ and $\overline{Z}_H$ to the bridge calibration potentiometer driver circuit of block 110 and an output from diode 432 to the fault indicator circuit of block 132.

Figure 14:
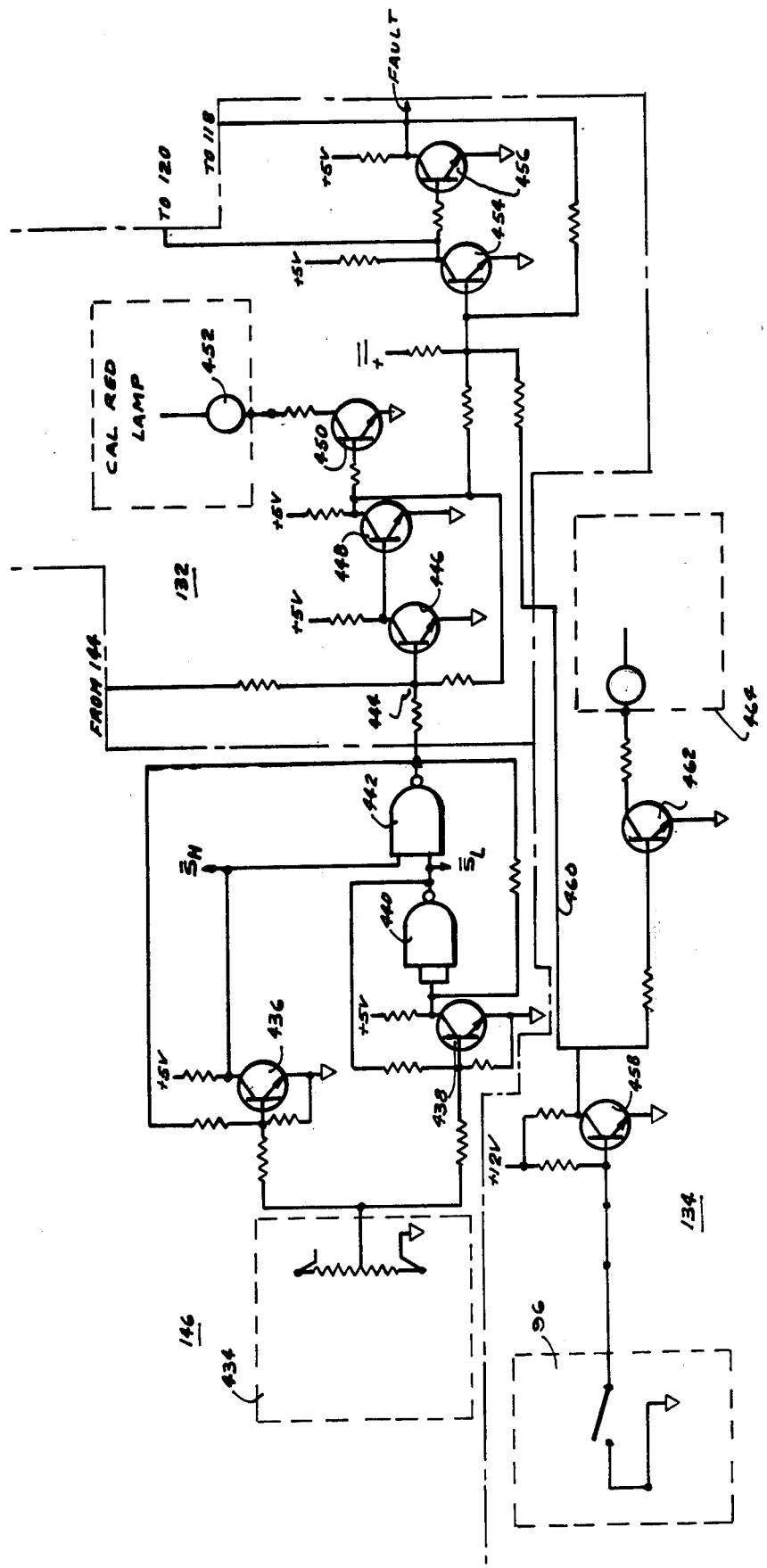
FIG. 14 is a schematic diagram of the second potentiometer travel limit detector circuit, the low-flow detector circuit and the calibration fault indicator driver circuit of the present invention.

FIG. 14 shows a schematic diagram of the MP2 travel limit detector circuit of block 146, fault indicator circuit of block 132 and sample low flow detector circuit of block 134. Circuit 146 is essentially the same as circuit 144. It contains a potentiometer 434 which is connected to the shaft of motorized potentiometer MP2. Transistors 436 and 438, along with gates 440 and 442, form an electronic limit on the travel of amplifier gain potentiometer MP2 and provide logic inputs $\overline{S}_L$ and $\overline{S}_H$ to the amplifier gain potentiometer drive circuit of block 114 and the FAULT indicator circuit of block 132.

The output from gate 430 of block 144 and of gate 442 in block 146 are combined at node 444 as an input to fault indicator circuit of block 132. Node 144 is connected to the base of transistor 446 which in turn drives transistor 448. Transistors 446 and 448 establish the logic for a CAL RED condition. The output circuit of trnsistor of 448 is connected to the base of transistor 450 which acts as a driver for the CAL RED lamp 452, located on the front panel of the component. Transistors 454 and 456 establish the logic for the fault condition and the output taken at the collector of transistor 456 constitutes the FAULT signal and is connected to block 118 among others. The output at the collector of transistor 454 is connected to circuit 120.

Block 134 has connected thereto, as an input, low flow switch 96 situated within the gas analyzer. This switch is connected to the base of transistor 458. The output circuit of transistor 458 causes the generation of a FAULT signal through connection with block 132 by means of line 460, which is connected to the base of transistor 454. Thus, a FAULT signal is generated when the flow within the gas analyzer is below a given value. The output circuit of transistor 458 is also connected to the base of a transistor 462 which acts as a driver for LOW FLOW lamp 464, which is present on the front panel of the control assembly.

Figure 15:
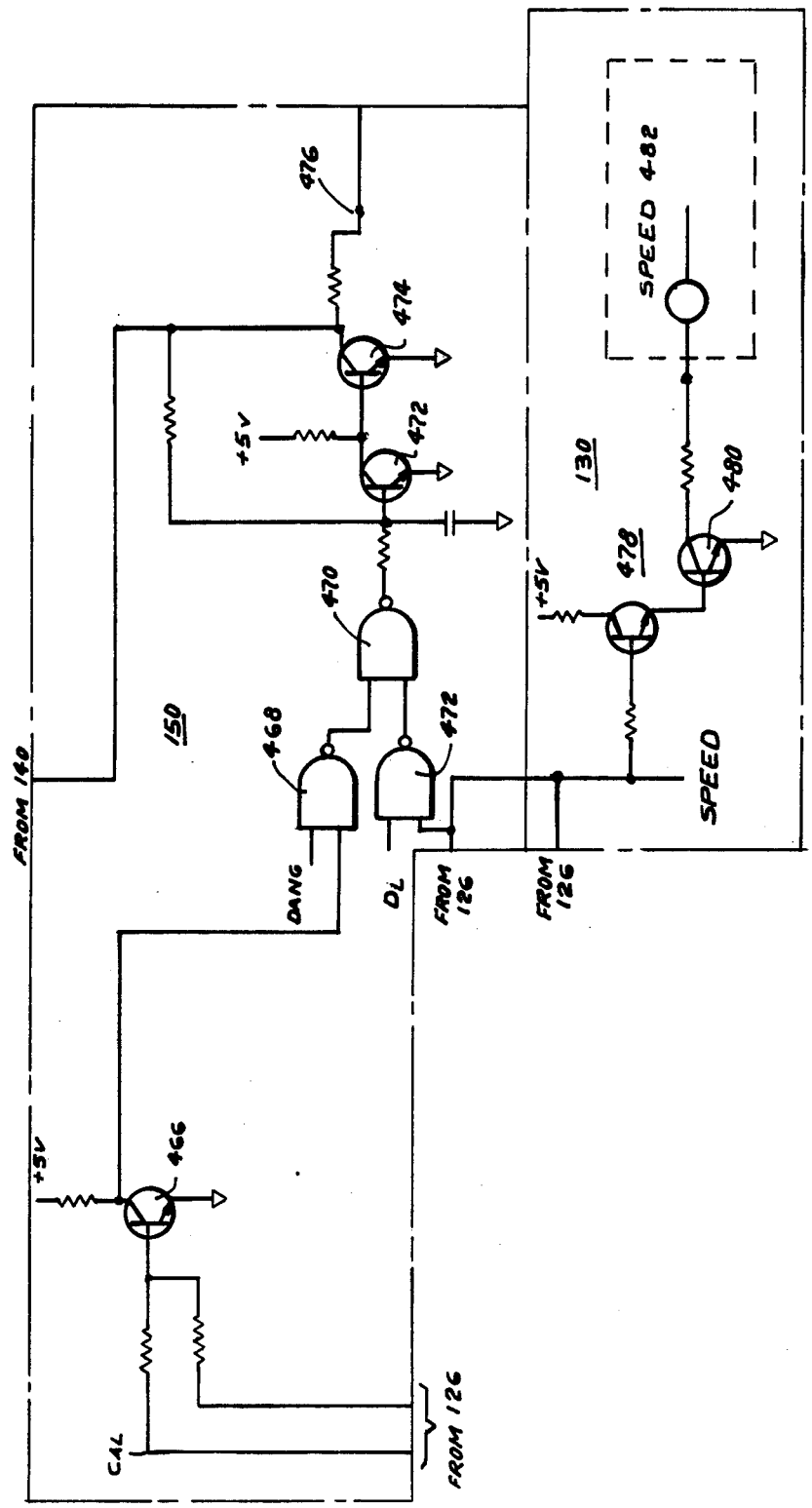
FIG. 15 is a schematic diagram of the emergency stop driver circuit and speed lamp driver circuit of the present invention.

FIG. 15 shows schematic diagrams of the emergency stop logic circuit 150 and speed lamp driver circuit 130. Block 150 receives the CAL signal (from block 116) at one of its inputs and this input is connected to the base of transistor 466, the collector of which is connected as an input to gate 468. The other input to gate 468 is the DANG signal from block 140. The output of gate 468 is connected to the input of gate 470. The other input of gate 470 is the output of a gate 472, the inputs of which are the $D_L$ and SPEED signals from blocks 106 and 126, respectively. Gates 468, 470 and 472 will cause transistor 474, the base of which is connected to the output of gate 470, and transistor 474, the base of which is connected to the collector of transistor 472, to latch to generate an "emergency stop" trigger signal at node 476, which is connected to the power supply assembly. When the danger signal is present during the LEL or SPEED mode functions or the $D_L$ signal is present when in the SPEED, TEST or CAL modes, the "emergency stop" signal is generated.

Block 130 contains the SPEED lamp driver circuit. This circuit has an input the SPEED signal, which is connected to the base of a transistor 478. The emittor of transistor 478 is connected to the base of transistor 480, which serves a driver for SPEED lamp 482.

Figure 16:
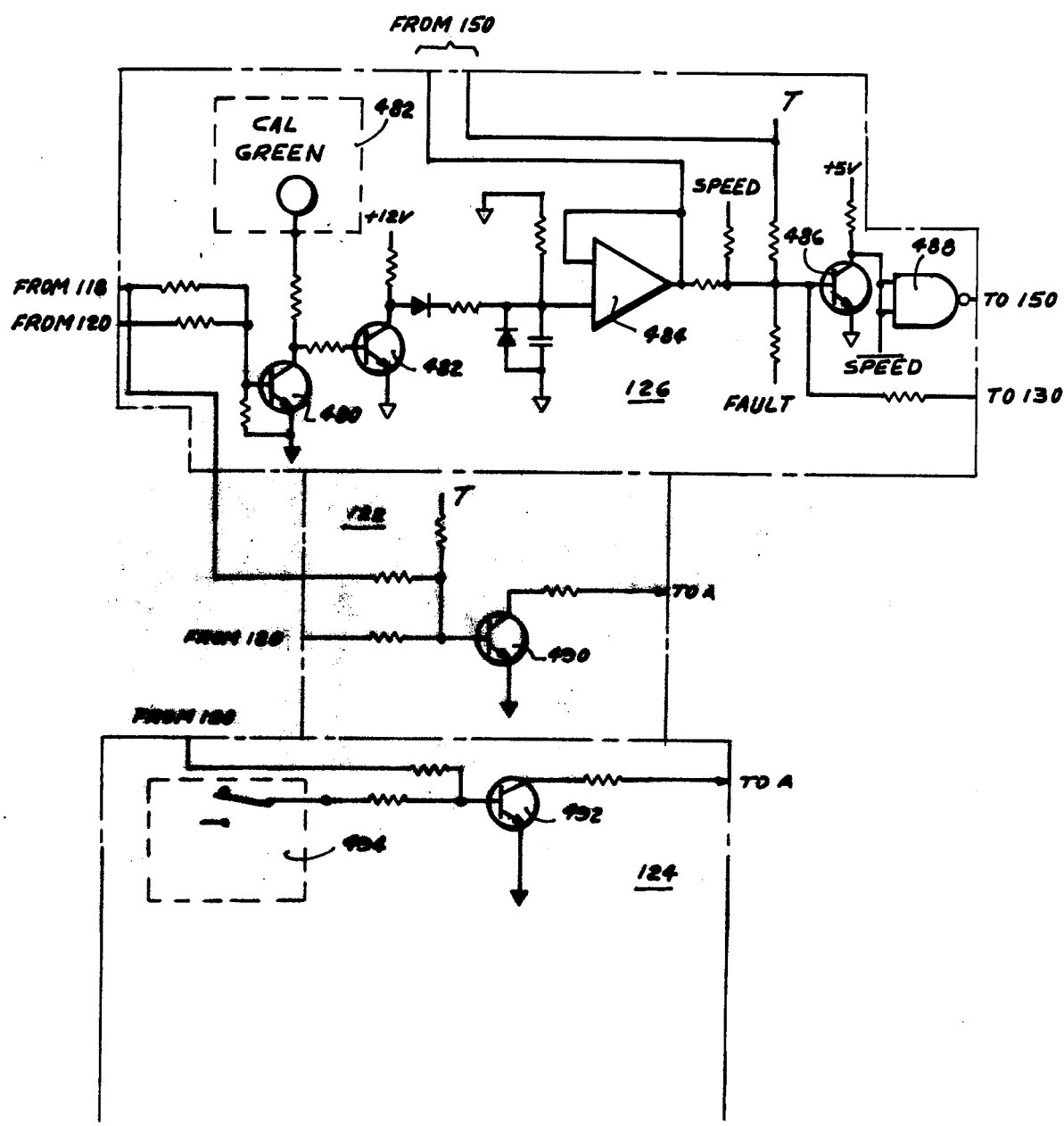
FIG. 16 is a schematic diagram of the calibration Green lamp indicator circuit, purge delay circuit, test-/sample selector driver circuit and air/methane selector drive circuit of the present invention.

FIG. 16 contains schematic diagrams of the purge delay circuit of block 126; test/sample selector drive circuit of block 122 and air/methane selector drive circuit of block 124. Block 126 receives inputs from blocks 118 and 120, which are connected to the base of transistor 480. Transistor 480 acts as the CAL GREEN lamp 482 driver. The collector of transistor 480 is connected to the base of a transistor 482, the collector of which is connected to one input of IC 484 (5B7741393 available from Fairchild). IC 484 acts as an integrator, generating a one minute delay to permit purging of the flame cell until transistor 486, the base of which is connected to the output of IC 484, turns off. When transistor 486 turns off, the SPEED signal is generated as an output thereof. The SPEED signal causes the system to return the LEL mode. At this point the calibration cycle is complete. The collector of transistor 486 is connected to a gate 488, the output of which is connected to one of the inputs of transistors 472 in block 150. A second input of this block is connected to the gate of transistor 478 of block 130.

Block 122, which is the test/sample selector driver circuit, receives an input from block 118 and a second input from block 120, which are combined and fed to the base of transistors 490. Transistors 490 drives solenoid 86 of gas analyzer A which selects the test or sample input to the flame cell.

Block 124 which is the air/methane selector drive circuit has an input from block 120 which is connected to the base of a transistor 492. The base of transistor 492 is also connected to a manual air/methane selector switch 494. Transistor 492 acts as a driver for solenoid 84 which selects the air or methane inputs to the gas analyzer flame cell.

It will therefore be appreciated, that the present invention relates to an LEL control which, under normal conditions, controls the position of an exhaust damper in accordance with the sensed solvent concentration level within the evaporation enclosure and the web speed. The system includes means for automatically, periodically calibrating the resistance bridge and amplifier therefor, during which time the damper position is controlled in accordance with the speed of the web alone. Calibration of the resistance bridge and amplifier takes place in two phases: first, zero solvent concentration gas is fed to the gas analyzer and the bridge circuit is calibrated at zero solvent concentration level by means of a motorized potentiometer; second, a gas of a known solvent level concentration is analyzed in the gas analyzer and the gain of the amplifier is calibrated in accordance with the known solvent concentration of the gas. Thus, the system is calibrated at both the zero and full scale levels. Thereafter, the system returns to its normal mode of operation. The system also includes means for continuously monitoring the solvent concentration level and for generating an "emergency stop" signal, to stop the press, in the event that the solvent level concentration within the evaporation enclosure reaches a dangerous level.

While only a single preferred embodiment of the present invention has been disclosed herein for purposes of illustration, it is obvious that many moidifications and variations could be made thereto. It is intended to cover all of these variations and modifications which fall within the scope of the invention as defined by the following claims.

I claim:

1. An LEL control for regulating the exhaust from an evaporation enclosure through which a solvent laden web passes comprising means operably connected to the enclosure for sensing the solvent concentration therein and for generating a first signal dependent thereupon, means operably associated with the web for sensing the speed thereof and for generating a second signal dependent thereupon, means for combining said first and said second signals to form a control signal, means for regulating said exhaust in accordance with said control signal, and means for calibrating said first signal generating means, said calibrating means comprising means for inhibiting the output of said first signal generating means during calibration.

2. The control of claim 1 wherein said calibration means comprises means for calibrating said first signal generating means at the zero setting and means for calibrating said first signal generating means at the full scale setting.

3. The control of claim 2 wherein said calibration means further comprises means for actuating said zero setting calibration means for a first given time interval and means for actuating said full scale setting calibration means for a second given time interval.

4. The control of claim 3 wherein said calibration means further comprises means for periodically generating a calibration initiation signal, said zero setting calibration actuation means being actuated by said initiation signal.

5. The control of claim 4 wherein said full scale setting calibration actuation means is actuated after said first given time interval.

6. The control of claim 5 wherein said calibration means is deactuated after said second time interval.

7. The control of claim 2 wherein said calibration means further comprises means for periodically generating a calibration initiation signal, said zero setting calibration means being actuated by said initiation signal.

8. The control of claim 1 wherein said first signal generating means comprises a gas analyzer and a bridge circuit, said bridge circuit comprising a variable resistance means for sensing the temperature in said analyzer, and amplification means for amplifying the output of said bridge circuit.

9. The control of claim 8 wherein said first signal generating means further comprises means for processing the output of said amplification means, said processing means comprising means for supplying a plurality of reference voltages, means for selecting one of said reference voltages and means for comparing said amplifier output with said selected reference voltage and producing an output in accordance with said comparison.

10. The control of claim 9 wherein said combining means comprises means for combining said comparison means output with said second signal to form said control signal.

11. The control of claim 2 wherein said first signal generating means comprises a gas analyzer and a bridge circuit, said bridge circuit comprising a variable resistance means for sensing the temperature in said analyzer, and amplification means for amplifying the output of said bridge circuit.

12. The control of claim 11 wherein said first signal generating means further comprises means for processing the output of said amplification means, said processing means comprising means for supplying a plurality of reference voltages, means for selecting one of said reference voltages and means for comparing said amplifier output with said selected reference voltage and producing an output in accordance with said comparison.

13. The control of claim 12 wherein said combining means comprises means for combining said comparison means output with said second signal to form said control signal.

14. The control of claim 11 wherein said zero setting calibration means comprises means for adjusting said bridge to the zero setting.

15. The control of claim 11 wherein said full scale calibration means comprises means for adjusting the gain of said amplification means to the full scale setting.

16. The control of claim 14 wherein said full scale calibration means comprises means for adjusting the gain of said amplification means to the full scale setting.

17. The control of claim 14 wherein said bridge circuit further comprises a potentiometer and wherein said zero setting calibrating means comprises means for adjusting said potentiometer to calibrate said bridge circuit to the desired zero setting.

18. The control of claim 1 wherein said calibration means further comprises means for periodically initiating calibration.

19. The control of claim 18 wherein said calibration initiation means comprises timing means for generating a calibration initiation signal at preset intervals.

20. The control of claim 1 further comprising means for generating an emergency stop signal when said first signal exceeds a preset level.

21. The control of claim 1 further comprising manually actuated means for inhibiting the output of said first signal generating means.

22. The control of claim 1 wherein said second signal generating means comprises a tachometer operably associated with said web.

23. The control of claim 1 wherein said first generating means comprises a gas analyzer, a first source of solvent free gas, a second source of known solvent concentration gas, valve means normally conditioned to connect said analyzer to said enclosure, and wherein said calibration means further comprises means for conditioning said valve means to connect said analyzer to said first source, during a zero setting phase of calibration and to said second source, during a full scale setting phase of calibration.

24. The control of claim 23 wherein said first signal generating means further comprises a bridge circuit said bridge circuit comprising a variable resistance means for sensing the temperature in said analyzer and a potentiometer, and means for amplifying the output of said bridge circuit.

25. The control of claim 1 wherein said first signal generating means comprises means for generating a signal which varies with the sensed solvent concentration, means for supplying a plurality of reference voltages, means for selecting one of said reference voltages, and means for comprising said preliminary signal and said selected reference voltage and for producing an output in accordance with said comparison.

26. The control of claim 25 wherein said combining means comprises means for combining said comparison means output with said second signal to form said control signal.

27. The control of claim 25 wherein said calibration means comprises means for calibrating said first signal generating means at the zero setting and means for calibrating said first signal generating means at the full scale setting.

28. The control of claim 27 wherein said zero setting calibraton means comprises means for adjusting said bridge to the zero setting.

29. The control of claim 27 wherein said full scale calibration means comprises means for adjusting the gain of said amplification means to the full scale setting.

30. The control of claim 25 wherein said reference voltages comprise a preset LEL reference voltage, a zero setting reference voltage and a full scale reference voltage.

31. The control of claim 30 wherein said calibration means comprises means for periodically initiating calibration.

32. The control of claim 31 wherein said calibrating means further comprises means, effective when calibration is initiated, for conditioning said reference voltage, such that said comparison means output represents the zero setting calibration signal.

33. The control of claim 32 wherein said calibration means further comprises timing means for generating a timing signal after a given time interval to initiate the full scale phase of calibration.

34. The control of claim 33 wherein said calibration means further comprises means, actuated upon receipt of said timing signal, for conditioning said reference voltage selecting means to select said full scale reference voltage, such that the output of said comparison means represents the full scale calibration signal.

35. The control of claim 34 wherein said calibration means further comprises means for adjusting the gain of said amplification means in accordance with said full scale calibration signal.

36. The control of claim 35 wherein said calibration means further comprises second timing means for generating a second timing signal after a given time interval to terminate calibration.

37. The control of claim 35 wherein said calibration means further comprises means, actuated upon receipt of said second timing signal, to actuate said reference voltage selecting means to select said preset LEL reference voltage and to deactuate said output inhibiting means.

38. The control of claim 25 wherein said first generating means comprises a gas analyzer, a first source of solvent free gas, a second source of known solvent concentration gas, valve means normally conditioned to connect said analyzer to said enclosure, and wherein said calibration means further comprises means for conditioning said valve means to connect said analyzer to said first source, during a zero setting phase of calibration and to said second source during a full scale setting phase of calibration.

39. The control of claim 38 wherein said reference voltages comprise a LEL reference voltage, a zero setting reference voltage and a full scale reference voltage.

40. The control of claim 39 wherein said calibration means comprises means, effective when calibration is initiated, to condition said valve means to select said first source and to condition said reference voltage selecting means to select said zero setting reference voltage such that said comparison means output represents the zero setting calibration signal.

41. The control of claim 40 wherein said calibration means further comprises timing means for generating a timing signal after a given time interval to initiate the full scale phase of calibration.

42. The control of claim 41 wherein said calibrating means further comprises means, actuated upon receipt of said timing signal, for conditioning said valve means to select said second source and for conditioning said reference voltage selecting means to select said full scale reference voltage such that the output of said comparison means represents the full scale calibration signal.

43. The control of claim 42 wherein said calibraton means further comprises means for adjusting the gain of said amplification means in accordance with said full scale calibration signal.

44. The control of claim 42 wherein said calibration means further comprises second timing means for generating a second timing signal after a given time interval to terminate calibration.

45. The control of claim 44 wherein said calibration means further comprises means actuated upon receipt of said second timing signal, to actuate said reference voltage selecting means to select said LEL reference voltage and to deactuate said output inhibiting means.

* * * * *